US011339365B2

(12) United States Patent
Nivala et al.

(10) Patent No.: US 11,339,365 B2
(45) Date of Patent: May 24, 2022

(54) NANOPORE SENSOR FOR ENZYME-MEDIATED PROTEIN TRANSLOCATION

(71) Applicant: The Regents of the University of California, Oakland, CA (US)

(72) Inventors: Jeffrey Matthew Nivala, Santa Cruz, CA (US); Douglas Benjamin Marks, Santa Cruz, CA (US); Mark Albert Akeson, Santa Cruz, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/378,448

(22) PCT Filed: Feb. 15, 2013

(86) PCT No.: PCT/US2013/026414
§ 371 (c)(1),
(2) Date: Aug. 13, 2014

(87) PCT Pub. No.: WO2013/123379
PCT Pub. Date: Aug. 22, 2013

(65) Prior Publication Data
US 2016/0032236 A1 Feb. 4, 2016

Related U.S. Application Data

(60) Provisional application No. 61/713,163, filed on Oct. 12, 2012, provisional application No. 61/599,754, filed on Feb. 16, 2012.

(51) Int. Cl.
| *C12Q 1/48* | (2006.01) |
| *B82Y 15/00* | (2011.01) |
| *C12M 1/00* | (2006.01) |
| *G01N 33/543* | (2006.01) |
| *G01N 33/487* | (2006.01) |

(52) U.S. Cl.
CPC ............... *C12M 47/06* (2013.01); *C12Q 1/48* (2013.01); *G01N 33/54366* (2013.01); *B82Y 15/00* (2013.01); *G01N 33/48721* (2013.01)

(58) Field of Classification Search
CPC .......... B82Y 15/00; C12M 47/06; C12Q 1/48; G01N 33/48721; G01N 33/54366
See application file for complete search history.

(56) References Cited

U.S. PATENT DOCUMENTS

| 5,795,782 A | 8/1998 | Church et al. | |
| 7,238,485 B2 | 7/2007 | Akeson et al. | |
| 7,846,738 B2 * | 12/2010 | Golovchenko | C12Q 1/6811 436/86 |
| 8,679,747 B2 | 3/2014 | Olasagasti et al. | |
| 8,916,684 B2 * | 12/2014 | Movileanu | C07K 14/245 530/350 |
| 2008/0287656 A1 * | 11/2008 | Peters | C12P 21/02 530/350 |
| 2011/0005918 A1 | 1/2011 | Akeson et al. | |
| 2011/0174625 A1 | 7/2011 | Akeson et al. | |
| 2011/0193249 A1 | 8/2011 | Chen et al. | |
| 2011/0311965 A1 * | 12/2011 | Maglia | G01N 33/48721 435/6.1 |
| 2012/0107802 A1 * | 5/2012 | Stoddart | C12Q 1/6869 435/6.1 |

FOREIGN PATENT DOCUMENTS

| CN | 1860370 A | 11/2006 |
| WO | 2002042496 A2 | 4/2003 |
| WO | 2010055307 A1 | 5/2010 |
| WO | 2010082860 A1 | 7/2010 |
| WO | 2010141468 A1 | 12/2010 |

OTHER PUBLICATIONS

Kravats et al. (Feb. 8, 2011) PNAS 108(6): 2234-2239.*
Kowalczyk et al. (2010) Nano Lett. 10(1): 324-328.*
Barkow et al. (2009) Chemistry & Biology 16:605-612. (Year: 2009).*
Harsman et al. (2010) J. Phys. Condens. Matter 22: 1-21. (Year: 2010).*
Erlandson et al. (2008) Nature 455: 984-988. (Year: 2008).*
Movileanu, L. (2009) Trends in Biotechnology 27(6): 333-341. (Year: 2009).*
Zimmer et al. (2008) Nature 455: 936-945. (Year: 2008).*
Holden et al. (2007) J. Am. Chem. Soc 129: 8650-8655. (Year: 2007).*
Talaga et al. (2009) J. Am. Chem. Soc. 131(26): 9287-9297. (Year: 2009).*
Bikwemu et al. (2010) J. Phys. Condens. Matter 22: 1-11. (Year: 2010).*
Merstorf et al., Wild Type, Mutant Protein Unfolding and Phase Transition Detected by Single-Nanopore Recording, ACS Chem. Biol. 2012, 7, 652-658, Pub. Jan. 12, 2012 (Year: 2012).*
Payet et al., Thermal Unfolding of Proteins Probed at the Single Molecule Level Using Nanopores, Anal. Chem. 2012, 84, 4071-4076, Pub. Apr. 9, 2012 (Year: 2012).*
Talaga et al., Single-Molecule Protein Unfolding in Solid State Nanopores, J. Am. Chem. Soc. 2009, 131, 9287-9297 (Year: 2009).*

(Continued)

*Primary Examiner* — Louise W Humphrey
*Assistant Examiner* — Srikanth Patury
(74) *Attorney, Agent, or Firm* — Brian E. Davy; Bozicevic, Field & Francis LLP

(57) ABSTRACT

Described herein is a device and method for translocating a protein through a nanopore and monitoring electronic changes caused by different amino acids in the protein. The device comprises a nanopore in a membrane, an amplifier for providing a voltage between the *cis* side and trans side of the membrane, and an NTP driven unfoldase which processed the protein to be translocated. The exemplified unfoldase is the ClpX unfoldase from *E. coli*.

17 Claims, 16 Drawing Sheets
Specification includes a Sequence Listing.

(56) References Cited

OTHER PUBLICATIONS

Tucker et al.,(The AAA+ superfamily—a myriad of motions, Current Opinion in Structural Biology 2007, 17:641-652 (Year: 2007).*
Enemark et al., On helicases and other motor proteins, Current Opinion in Structural Biology 2008, 18:243-257 (Year: 2008).*
Derrington et al., Nanopore DNA sequencing with MspA, 16060-16065 | PNAS | Sep. 14, 2010 | vol. 107 | No. 37 (Year: 2010).*
Kravats et al., Unfolding and translocation pathway of substrate protein controlled by structure in repetitive allosteric cycles of the ClpY ATPase, 2234-2239 | PNAS | Feb. 8, 2011 | vol. 108 | No. 6 (Year: 2011).*
Martin et al., Pore loops of the AAA+ ClpX machine grip substrates to drive translocation and unfolding, Nature Structural & Molecular Biology, vol. 15, No. 11, Nov. 2008 (Year: 2008).*
Stefureac et al., Nanopore Analysis of a Small 86-Residue Protein, Small, 2008, 4, No. 1, 59-63 (Year: 2008).*
CLPX Gene, GeneCard Webpage (Year: 2021).*
Singh et al., Unfolding and internalization of proteins by the ATP-dependent proteases ClpXP and ClpAP, PNAS, Aug. 1, 2000, vol. 97, No. 16, pp. 8898-8903 (Year: 2000).*
Benner, S., et al., "Sequence-specific detection of individual DNA polymerase complexes in real time using a nanopore", Nat Nanotechnol. (2007) 2(11):718-724.
Branton, D., et al., "The potential and challenges of nanopore sequencing", Nature Biotechnology (2008) 26(10):1146-1153.
Cockroft, S., et al., "A Single-Molecule Nanopore Device Detects DNA Polymerase Activity With Single-Nucleotide Resolution", J Am Chem Soc (2008) 130(3):818-820.
Harsman, A., et al., "Protein conducting nanopores", J. Phys. Condens. Matter (2010) 22(45):454102.
Howorka, S., et al., "Nanopores as protein sensors", Nature Biotechnology (2012) 30(6):506-507.
Kravats, S., et al., "Unfolding and translocation pathway of substrate protein controlled by structure in repetitive allosteric cycles of the ClpY ATPase", PNAS (2011) 108(6):2234-2239.
Maillard, R., et al., "ClpX(P) Generates Mechanical Force to Unfold and Translocate Its Protein Substrates", Cell (2011) 145(3):459-469.
Martin, A., et al., "Rebuilt AAA+ motors reveal operating principles for ATP-fuelled machines", Nature (2005) 437:1115-1120.
Nivala, J., et al., "Unfoldase-mediated protein translocation through an α-hemolysin nanopore", Nature Biotechnology (2013) 31(3):247-250.
Nivala, J., et al., "Discrimination among Protein Variants Using an Unfoldase-Coupled Nanopore", ACS NANO (2014)8(12):12365-12375.
Nouwen, N., et al., "Charged Amino Acids in a Preprotein Inhibit SecA-Dependent Protein Translocation", J. Mol. Biol. (2009) 386(4):1000-1010.
Talaga, D., et al., "Single-molecule Protein Unfolding in Solid State Nanopores", Journal of the American Chemical Society (2009) 131(26):9287-9297.
Vercoutere, W., et al., "Rapid discrimination among individual DNA hairpin molecules at single-nucleotide resolution using an ion channel", Nature Biotechnology (2001) 19:248-252.
Zhao, Q., et al., "Detecting SNPs using a Synthetic Nanopore", Nano Lett. (2007) 7(6):1680-1685.
Zuber, P., et al., "The Role of the Hsp100/Clp Family of Proteins in Prokaryotic Development", Journal of Microbiology (2000) 38(4):193-202.
Kim et al., "Dynamics of Substrate Denaturation and Translocation by the ClpXP Degradation Machine" Molecular Cell, vol. 5, 639-648, Apr. 2000.

* cited by examiner

S1    S2-35    S2-148

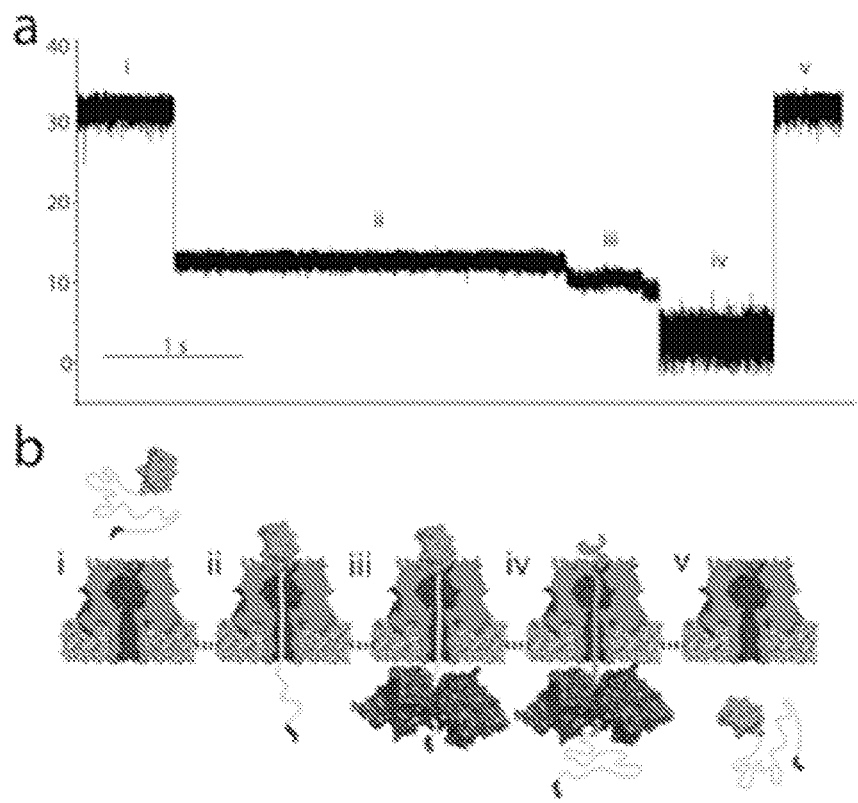
Fig. 2A-B

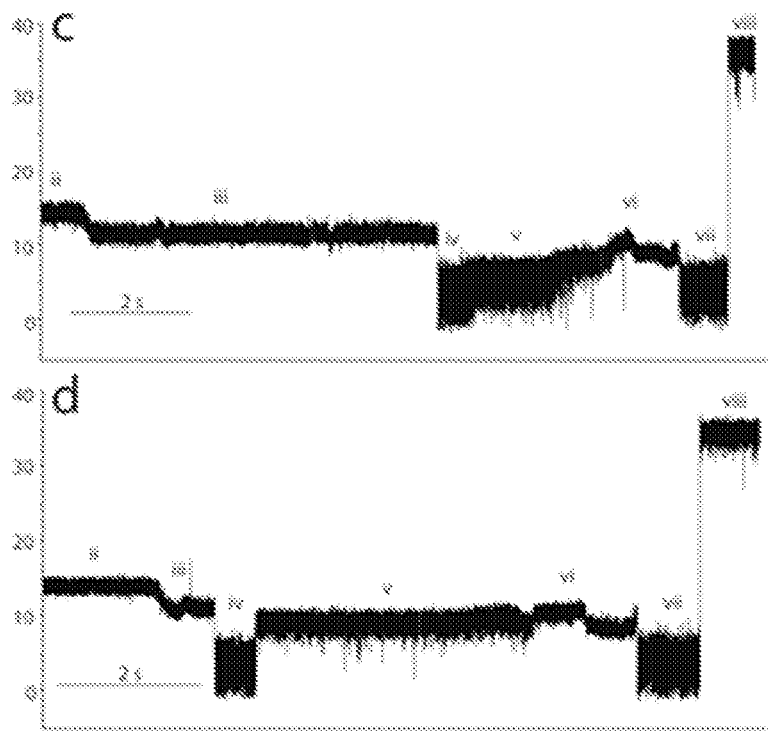
Fig. 2C-D

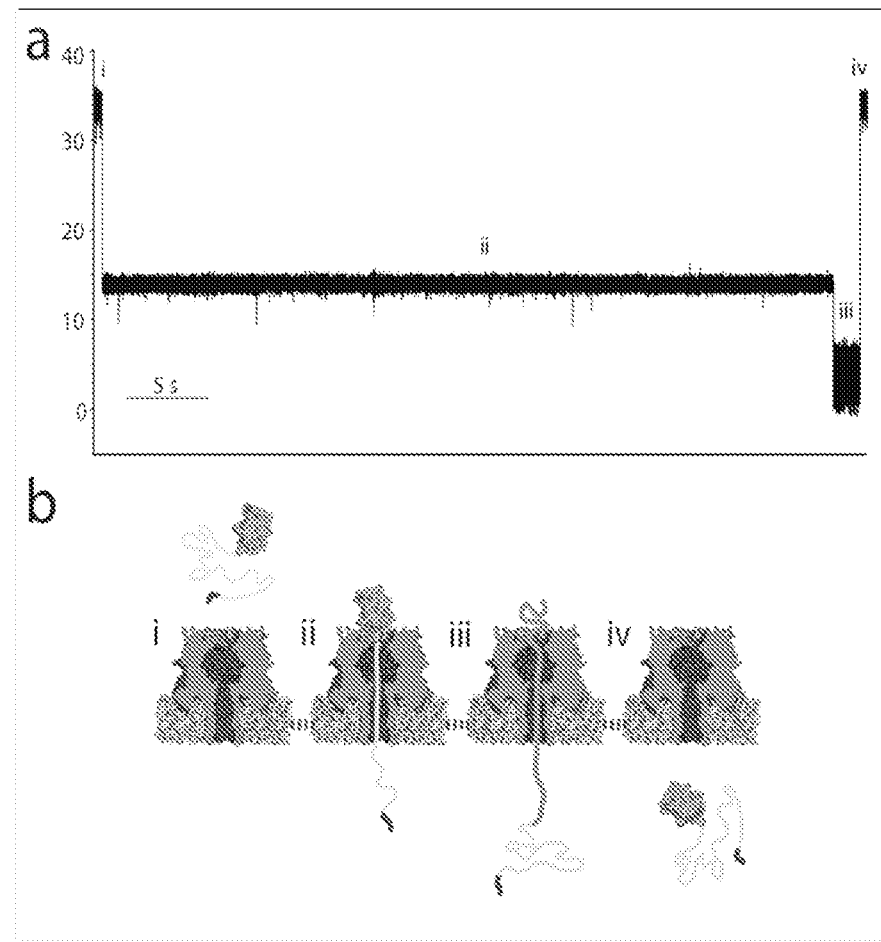
Fig. 4A-B

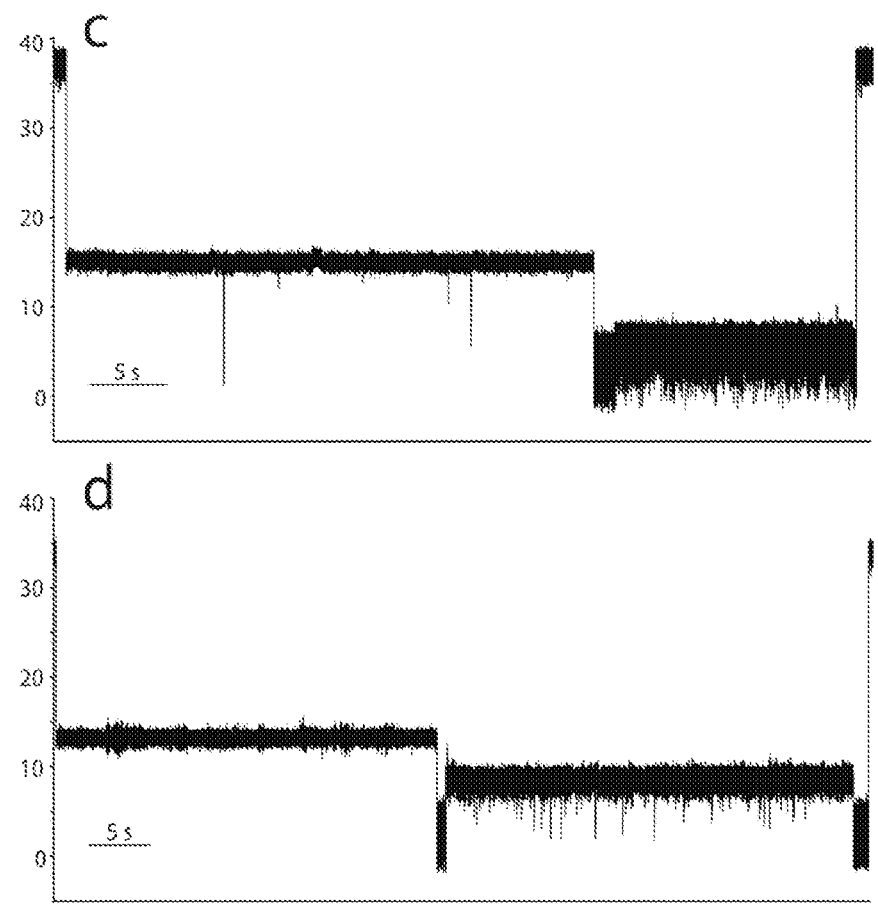
Fig. 4C-D

NANOPORE SENSOR FOR ENZYME-MEDIATED PROTEIN TRANSLOCATION

CROSS-REFERENCE TO RELATED APPLICATIONS

This application claims priority from U.S. Provisional Patent Application No. 61/599,754, filed Feb. 16, 2012, by Jeffrey Nivala, entitled "Unfolding and Translocation of Proteins Through a Nanopore Sensor and Methods of Use", and U.S. Provisional Patent Application No. 61/713,163, filed Oct. 12, 2012 by Jeffrey Nivala et al., entitled "Nanopore Sensor for Enzyme-Mediated Protein Translocation," both of which are hereby incorporated by reference in their entirety, and is a national stage application of PCT application PCT/US2013/026414, having an international filing date of 15 Feb. 2013, the disclosure of which is incorporated herein by reference in its entirety.

STATEMENT OF GOVERNMENTAL SUPPORT

This invention was made with government support under contract R01HG006321 awarded by the National Institutes of Health. The government has certain rights in this invention.

REFERENCE TO SEQUENCE LISTING, COMPUTER PROGRAM, OR COMPACT DISK

A sequence listing will be submitted upon filing of a utility patent application.

BACKGROUND OF THE INVENTION

1. Field of the Invention

The present invention relates to the field of single molecule protein analysis and also to the field of nanopore analysis.

2. Related Art

Presented below is background information on certain aspects of the present invention as they may relate to technical features referred to in the detailed description, but not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

Nanopores have been used for various biosensing applications, the most popular of which has been DNA analysis (e.g. sequencing). Similarly, nanopore sequencing of proteins has also been envisioned. However, unlike nucleic acids, proteins are generally not uniformly charged (making it difficult to drive translocation via an applied voltage) and they also fold into complex, large, and stable structures that cannot transverse a nanopore's aperture. More specifically, the reasons that protein sequencing is technically more challenging than DNA sequencing include: i) twenty amino acids must be discerned for protein sequencing compared to four nucleotides for DNA sequencing (not including post-translational and epigenetic modifications); ii) both tertiary and secondary structures must be unfolded to allow the denatured protein to thread through the nanopore sensor in single file order; and iii) processive unidirectional translocation of the denatured polypeptide through the nanopore electric field must be achieved despite non-uniform charge along the polypeptide backbone.

The use of nanopores to sequence biopolymers was proposed more than a decade ago (Pennisi, E. Search for pore-fection. *Science* 336, 534-537 (2012), Church, G. M., Deamer, D. W., Branton, D., Baldarelli, R. & Kasianowicz, J. Characterization of individual polymer molecules based on monomer-interface inter-action. U.S. Pat. No. 5,795,782 (1998)).

Recent advances in enzyme-based control of DNA translocation (Cherf, G. M., Lieberman, K. R., Rashid, Hytham, R., Lam, C. E., Karplus, K. & Akeson, M. Automated forward and reverse ratcheting of DNA in a nanopore at 5-Å precision. *Nat. Biotechnol.* 30, 344-348 (2012).), and in DNA nucleotide resolution using modified biological pores (Manrao, E. A., Derrington, I. M., Laszlo, A. H., Langford, K. W., Hopper, M. K., Gillgren, N., Pavlenok, M., Niederweis, M., & Gundlach, J. H. Reading DNA at single-nucleotide resolution with a mutant MspA nanopore and phi29 DNA polymerase. *Nat. Biotechnol.* 30, 349-353 (2012)), have set the stage for a nanopore DNA sequencing instrument anticipated for commercial release in late 2012 (Hallam, K. "Oxford nanopore to sell tiny DNA sequencer," Bloomberg, published online 17 Feb. 2012, Hayden, E. Nanopore genome sequencer makes its debut. Nature, published online 17 Feb. 2012).

Although protein movement through nanopores has been established (Mohammad, M. M., Prakash, S., Matouschek, A., & Movileanu, L. Controlling a single protein in a nanopore through electrostatic traps. *J. Am. Chem. Soc.* 130, 4081-4088 (2008), Talaga, D. S. & Li, J. Single-molecule protein unfolding in solid state nanopores. *J. Am. Chem. Soc.* 131, 9287-9297 (2009), Merstorf, C., Cressiot, B., Pastoriza-Gallego, M., Oukhaled, A., Betton, J., Auvray, L. & Pelta, J. Wild type, mutant protein unfolding and phase transition detected by single-nanopore recording. *ACS Chem. Biol.* 7, 652-658 (2012)), a technique to unfold proteins for controlled, sequential translocation has until now not been demonstrated.

BRIEF SUMMARY OF THE INVENTION

The following brief summary is not intended to include all features and aspects of the present invention, nor does it imply that the invention must include all features and aspects discussed in this summary.

The present invention provides a device for translocating a protein through a nanopore, comprising: a membrane having nanopore therein, said membrane separating a chamber into a cis side and a trans side, wherein the protein is to be added to the cis side and translocated through the nanopore to the trans side; and a protein translocase enzyme, on one side of said chamber, which binds to and translocates the protein through the nanopore. Translocation will occur in a sequential order, that is, in a defined sequence of amino acid residues passing into the nanopore, which will generally follow the primary amino acid sequence of the protein.

The present invention also provides a device for translocating a protein through a nanopore, comprising: a nanopore in a membrane, said membrane separating a fluidic chamber into a cis side and a trans side, wherein a protein to be translocated is added to the cis side and is translocated through the nanopore to the trans side; a circuit for providing a voltage between the cis side and the trans side and for measuring ionic current flowing through the nanopore; and a specific enzyme, such as a protein translocase and/or an NTP driven unfoldase added to the fluid chamber, e.g. by being allowed to become attached to said nanopore on the *cis* side, or by addition in solution to the trans side.

In one embodiment of the present invention, the nanopore is defined by a pore protein. In one preferred embodiment, the pore protein is α-hemolysin.

In another embodiment of the present invention, the protein translocase is an NTP driven unfoldase which operates on the protein molecule to be translocated. In one preferred embodiment, the NTP driven unfoldase is an AAA+ enzyme. In an especially preferred embodiment, the AAA+ enzyme is *E. coli* ClpX.

In another embodiment of the present invention, the circuit for detection of protein translocation comprises a patch clamp amplifier applying a positive voltage to the trans side. The patch clamp amplifier maintains a constant voltage and measures changes in current. In a preferred embodiment, the device comprises a computer, attached to the patch clamp amplifier, for rapidly recording changes in ionic current through the nanopore. As the protein passes through the nanopore an ionic current signature is obtained which can detect on the order of 1 to 100,000 fluctuations per second, providing information about individual amino acids translocating through the pore. For example, recording at 100 kHz can be used to produce one data point every 10 µS.

In another embodiment of the present invention, a system for translocating a protein through a nanopore is provided, comprising a nanopore in a membrane separating a fluidic chamber into a *cis* side and a trans side, wherein a protein to be translocated is added to the *cis* side and is translocated through the nanopore to the trans side; said fluidic chamber comprising an ionic buffer containing an enzyme cofactor such as NTP (nucleoside 5'-triphosphate) and a non-denatured protein to be translocated on the *cis* side; a circuit for providing a voltage between the *cis* side and the trans side and measuring ionic current flowing through the nanopore; and a protein translocase such as an NTP driven unfoldase in solution in the chamber on the *cis* side.

In an alternative embodiment of the present invention, the nanopore is defined by a pore protein such as a multimeric pore protein and the protein translocase such as an NTP driven unfoldase is attached to the multimeric pore protein. The protein translocase may be covalently or non-covalently attached to the pore protein, and may be on the *cis* side, the trans side or both sides of the membrane and pore protein.

In another embodiment of the present invention, the protein to be translocated is a non-denatured protein (i.e. in its native state) and, further, comprises an exogenous sequence comprising a targeting domain for the protein to be targeted to pass through the nanopore and contact the NTP driven unfoldase. In a preferred embodiment, the NTP driven unfoldase is ClpX and the nanopore protein is α-hemolysin. The targeting domain in the exogeneous sequence serves to guide the protein to the nanopore. The targeting domain may be configured to be affected by the voltage across the nanopore. In one preferred embodiment, the targeting domain comprises at about 5-30 negatively charged amino acids and is drawn to the positive side of the chamber by the voltage gradient.

The present invention also provides a method for translocating a non-denatured protein through a nanopore, comprising the steps of: providing a device for translocating a protein through a nanopore, said device comprising a nanopore in a membrane separating a fluidic chamber into a *cis* side and a trans side, wherein a protein to be translocated is added to the *cis* side and is translocated through the nanopore to the trans side; a circuit for providing a voltage between the *cis* side and the trans side and measuring ionic current flowing through the nanopore; and a protein translocase in solution on the trans side; adding to said fluidic chamber a buffer containing NTPs (where the translocase is NTP-driven); optionally adding a non-denatured protein to the *cis* side; allowing the non-denatured protein to be captured or threaded through the nanopore (e.g. by charge) so that it can contact the protein translocase; and measuring ionic current changes caused by translocation of the non-denatured protein through the nanopore.

In one embodiment of the present invention, the step of measuring current changes comprises measuring current changes for states of (i) open channel in the nanopore, (ii), capture of the nondenatured protein by the nanopore, and (iii) passage of a protein from (ii) through the nanopore. In a preferred embodiment, the measuring comprises detecting differences between states (i), (ii) and (iii). In another preferred embodiment, the measuring comprises measuring differences during state (iii) caused by amino acid structure of the protein passing through the nanopore. In another preferred embodiment, the nanopore is defined by a pore protein. In a yet more preferred embodiment, the pore protein is α-hemolysin. In another preferred embodiment, the NTP driven unfoldase is attached to the pore protein. In a more preferred embodiment, the NTP driven unfoldase is an AAA+ enzyme. In a yet more preferred embodiment, the AAA+ enzyme is ClpX. In another embodiment, the circuit comprises a patch clamp amplifier applying a constant voltage between the *cis* chamber and the trans chamber.

In certain aspects of the present invention, the nanopore is defined by α-hemolysin or another multimeric pore protein. The pore protein does not need to be functionalized; that is it may be used as the protein exits in its native environment; it does not need to have any molecular structures added to it to attach or bind the protein being translocated. That is, it may be generic for translocation of any protein sequence, and does not specifically bind to or recognize the protein to be translocated. The protein to be translocated is also preferably in a native form. It may, in certain embodiments of the present invention, have attached to it a molecular structure for improving "threading" of the protein through the nanopore. In certain aspects of the present invention, the protein to be translocated comprises an exogeneous sequence comprising a targeting domain for the protein translocase. The targeting domain may comprise at least about 10-30 negatively charged amino acids, e.g. 30-100 glutamate or aspartate residues, or other negatively charged synthetic monomers, e.g. dextran sulfate, located at an amino or carboxy terminus of the protein to be translocated.

In certain aspects of the present invention, the protein to be translocated is translocated in its native state, that is without being denatured or otherwise unfolded; the protein translocate serves to unfold the protein as it traverses the voltage gradient across the nanopore.

BRIEF DESCRIPTION OF THE DRAWINGS

FIG. 2A, 2B is a diagrammatic representation and plot that shows the ionic current traces during ClpX-mediated protein translocation.

FIG. 2C is a trace that shows the ionic current traces during protein S2-35 translocation.

FIG. 2D is a trace that shows the ionic current traces during protein S2-148 translocation.

FIG. 4 is a diagrammatic representation and current trace that shows the ionic current traces during voltage-mediated protein translocation without the presence of ClpX in the trans solution. After a highly variable capture duration (<5 sec->2 min), all substrates tested will eventually unfold and translocate due to the applied voltage. No ramping states are observed, detailed signal features are lost from S2-35 and S2-148 linker states, and all states have more widely distributed durations as compared to ClpX-mediated events. FIG. 4A shows the ionic current traces during voltage-mediated S1 translocation. Compared to FIG. 2A, state iii is absent and state iv has a longer and more variable duration on average. FIG. 4B illustrates the model of voltage-mediated protein translocation. FIG. 4B shows four cartoon structures, i. through iv. Cartoons i-iv correspond to ionic current states i-iv in FIG. 4A. FIG. 4C shows the ionic current traces during voltage-mediated S2-35 translocation. Ramping of states iii and vi are absent and resolution of state v (FIG. 2C) is diminished. FIG. 4D shows the ionic current traces during voltage-mediated S2-148 exhibits similar behavior to S2-35 with the corresponding states omitted (FIG. 2D).

DETAILED DESCRIPTION OF THE PREFERRED EMBODIMENT

Overview

Described herein is a device, method, and system for translocating an individual protein through a nanopore so as to enable information about the amino acid content of the protein to be obtained through electronic signals reflecting passage of an individual protein through an individual nanopore. By providing a nanopore in a membrane, a voltage between the cis side and trans side of the membrane, and a protein translocase, the present device achieves the enzyme-controlled unfolding and translocation of native proteins through a nanopore sensor using the protein translocase in such a way that circuitry between the cis side and the trans side can monitor and record signals indicative of the amino acid content of the protein, e.g. amino acid sequence. For practical purposes, an array of nanopores and circuits can be provided. These can be in a single chamber or in multiple chambers.

Figure 1A:
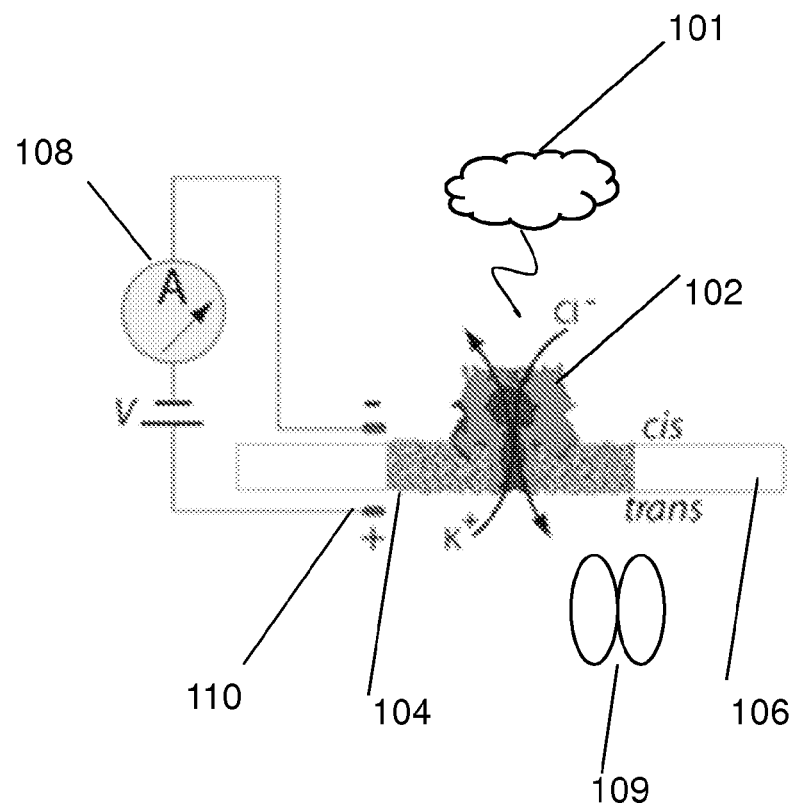
FIG. 1A is a diagrammatic drawing (cartoon) of a nanopore sensor with a single α-HL (α-hemolysin) pore embedded in a lipid bilayer.
Figure 1B:
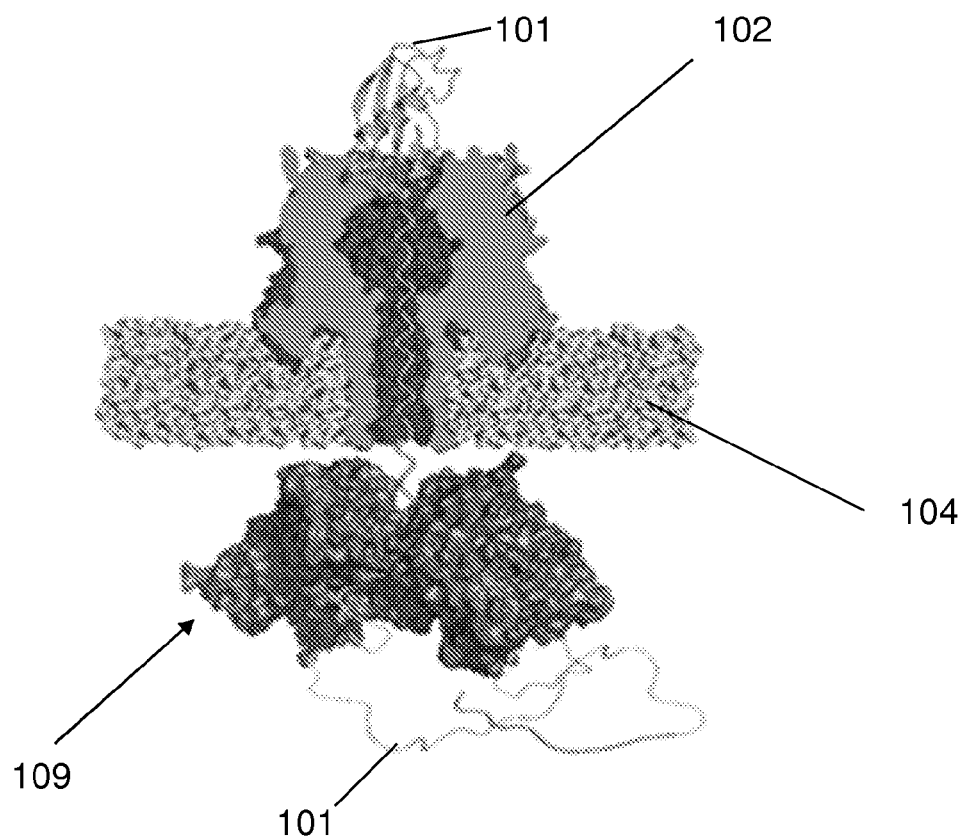
FIG. 1B is a diagrammatic drawing that shows a protein captured in the nanopore.
Figure 1C:
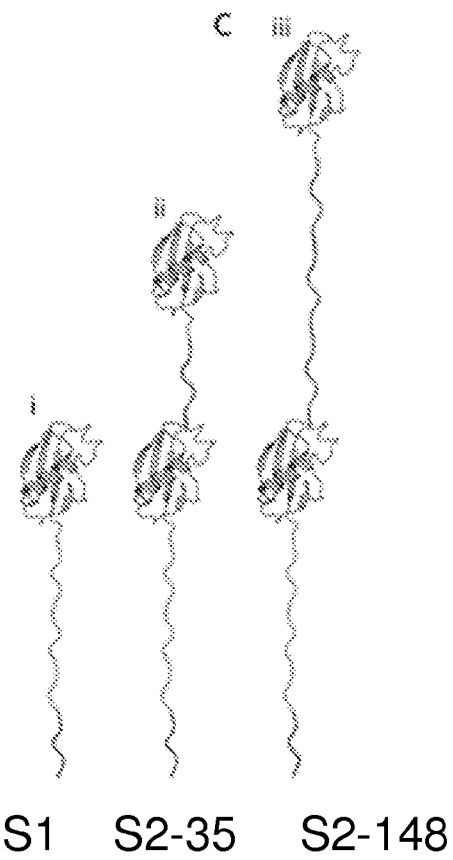
FIG. 1C is a diagrammatic drawing that shows the engineered proteins used in the present examples for translocation.

Referring now to FIG. 1A, the present device operates to translocate a protein 101 and comprises a pore protein 102 (α-hemolysin) embedded in a lipid bilayer 104 that is comprised in an ~25 μm aperture in a membrane 106 separating a fluid compartment into a cis side, containing the protein 101, and a trans side, to which the protein 101 is going to be translocated through the pore 102. The device includes a controllable amplifier 108 for applying a constant voltage between a positive electrode 110 on the trans side and a negative electrode on the cis side. A protein translocase 109 is present on the trans side of the chamber. Amplifier 108 also provides a circuitry for detecting and, preferably, recording changes in ionic current (i.e. flow of ions such as the depicted Cl$^-$ and K$^+$) that take place very rapidly as the protein 101 translocates. In the examples data were collected at 100 kHz, but high speed data sampling devices are known and may be used (e.g. 200 MHz Model 7150 from Pentek, Inc). FIG. 1B shows a detailed view of pore protein 102 in the lipid bilayer 104 and also shows the protein translocase 109 on the trans side, which is acting on protein 101 which in the cartoon is on both sides of the pore 102. As shown in FIG. 1C, a model protein bearing a Smt3 domain at its amino-terminus is coupled by a charged flexible linker to an ssrA tag at its carboxy-terminus. The charged, flexible tag is threaded through the nanopore into the trans-side solution, while the folded Smt3 domain at this point prevents complete translocation of the captured protein. ClpX present in the trans solution binds the C-terminal ssrA sequence. Fueled by ATP hydrolysis, ClpX translocates along the protein tail toward the channel, and subsequently catalyzes unfolding and translocation of the Smt3 domain through the pore.

Demonstrated in the examples below is enzymatic control of protein unfolding and translocation through the α-hemolysin nanopore. Segments of each protein were discerned based on amino acid composition as they passed through the circa 50-Angstrom-long transmembrane pore lumen (nanopore). The enzyme used in this translocation is selected and controlled to provide protein sequence information. The enzyme is selected from a class of enzymes termed generally herein "protein translocases," referring to the ability of such enzymes to cause physical movement relative to a substrate. Included within the term as used herein is a class of enzymes often referred to as "unfoldases," in that they catalyze the unfolding of a native protein without affecting the primary structure, i.e. the primary sequence of the protein.

The invention may be carried out in a conventional apparatus for polynucleotide analysis, such as an array or a chip. The apparatus may be any of those described in International Application No. PCT/GB08/004127 (published as WO 2009/077734), PCT/GB10/000789 (published as WO 2010/122293), International Application No. PCT/GB10/002206 (WO 2011/067559) or International Application No. PCT/US99/25679 (published as WO 00/28312). As will become apparent from the description below, the protein is translocated as a single polypeptide sequence, wherein individual amino acids pass sequentially through the pore.

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

Ranges: For conciseness, any range set forth is intended to include any sub-range within the stated range, unless otherwise stated. As a non-limiting example, a range of 120 to 250 is intended to include a range of 120-121, 120-130, 200-225, 121-250 etc. The term "about" has its ordinary meaning of approximately and may be determined in context by experimental variability. In case of doubt, "about" means plus or minus 5% of a stated numerical value.

The term "nanopore" is used herein to refer to any small hole or channel of the order of 0.5 to 10 nanometers in internal diameter. The term "nanopore" includes both biological (e.g. α-hemolysin) or artificial nanopores. The present nanopores can vary in dimensions, for example it can have a diameter of between about 0.5 nm and 10 nm in size. For example, the diameter can be about 0.5 nm, 1 nm, 1.25 nm, 1.5 nm, 1.75 nm, 2 nm, 2.25 nm, 2.5 nm, 2.75 nm, 3 nm, 3.5 nm, 4 nm, 4.5 nm, 5 nm, 6 nm, 7 nm, 8 nm, 9 nm, 10 nm, or any dimension there between. Biological nanopores can be created by pore proteins. Artificial nanopores can be made by micromolding or drilling. They also can be made by etching a somewhat larger hole (several tens of nanometers) in a piece of silicon, and then gradually filling it in using ion-beam sculpting methods which results in a much smaller diameter hole.

The term "pore protein" is used herein to refer to pore-forming proteins (PFPs) which assemble into ring-like structures in the vicinity of the target membrane to expose sufficient hydrophobicity to drive spontaneous bilayer insertion. Pore proteins are typically (but not exclusively) produced by bacteria, such C. septicum and S. aureus. PFPs can be alpha-pore-forming toxins, such as Cytolysin A of E. coli; or beta-pore-forming toxins, such as α-hemolysin and Panton-Valentine leukocidin (PVL); or binary toxins, such as Anthrax toxin; or cholesterol-dependent cytolysins (CDCs), such as Pneumolysin; or Small pore-forming toxins, such as Gramicidin A. A preferred pore protein is α-hemolysin.

The term "α-hemolysin" is used herein to refer to a pore-forming toxin from the bacterium, Staphylococcus aureus. α-hemolysin consists mostly of beta-sheets (68%) with only about 10% alpha-helices. The hla gene on the S. aureus chromosome encodes the 293 residue protein monomer, which forms heptameric units on the cellular membrane to form a complete beta-barrel pore. This structure allows the toxin to perform its major function, development of pores in the cellular membrane.

The term "membrane" is used herein to refer to a thin, film-like structure. Membranes can be generally classified into synthetic membranes and biological membranes. Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic layer may be a monolayer or a bilayer. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450).

The term "lipid bilayer" is used herein to refer to a thin polar membrane made of two layers of lipid molecules, arranged so that the hydrophilic phosphate heads point "out" to the water on either side of the bilayer and the hydrophobic tails point "in" the core of the bilayer. The lipid bilayers are usually a few nanometers in width, and they are impermeable to most charged water-soluble molecules. Lipid bilayers are large enough structures to have some of the mechanical properties of liquids or solids. The area compression modulus Ka, bending modulus Kb, and edge energy, can be used to describe them. Solid lipid bilayers also have a shear modulus, but like any liquid, the shear modulus is zero for fluid bilayers. Lipid bilayers can also be supported by solid substrates having apertures, such as heat shrink tubing, fused silica, borosilicate glass, mica, and oxidized silicon. Lipids may be applied, e.g., through Langmuir-Blodgett technique, vesicle fusion processes or the combination of the two.

The term "NTP" is used herein to refer to nucleoside triphosphate, a molecule containing a nucleoside bound to three phosphates, making it a nucleotide. NTP can be adenosine triphosphate (ATP), guanosine triphosphate (GTP), cytidine triphosphate (CTP), 5-methyluridine triphosphate ($m^5$UTP), uridine triphosphate (UTP), deoxyadenosine triphosphate (dATP), deoxyguanosine triphosphate (dGTP), deoxycytidine triphosphate (dCTP), deoxythymidine triphosphate (dTTP) or deoxyuridine triphosphate (dUTP). "NTP" also refers to other less abundant NTPs, such as intermediates of nucleotide metabolism, including less common natural The term "NTP driven unfoldase" is used herein to refer to an NTP-dependent enzyme that catalyzes protein unfolding. The very common NTP driven unfoldases are ATP-dependent proteases, such as proteasomal ATPases, AAA proteases, or AAA+ enzymes (defined below); membrane fusion proteins, such as NSF (N-Ethylmaleimide-sensitive fusion protein)/Sac18p (N-Ethylmaleimide-sensitive fusion protein homologue in yeast) or p97/VCP/Cdc48p (97-kDa valosin-containing protein); Pex1p and Pex6p (peroxisomal ATPase); Katanin and SKD1 (Vps4p homolog in mouse)/Vps4p (Vacuolar protein sorting 4 homolog in yeast); Dynein (motor protein); DNA replication proteins, such as ORC (origin recognition complex), Cdc6 (cell division control protein 6), MCM (minichromosome maintenance protein), DnaA, or RFC (replication factor C)/clamp-loader; RuvB (holliday junction ATP-dependent DNA helicase RuvB, EC=3.6.4.12); TIP49a/TIP49 and TIP49b/TIP48 (eukaryotic RuvB-like protein).

The term "AAA+ enzyme" is used herein to refer to the AAA+ superfamily of enzymes. AAA+ is an abbreviation for ATPases Associated with diverse cellular Activities. They share a common conserved module of approximately 230 amino acid residues. This is a large, functionally diverse protein family belonging to the AAA+ superfamily of ring-shaped P-loop NTPases, which exert their activity through the energy-dependent remodeling or translocation of macromolecules. Examples include ClpAP, ClpXP, ClpCP, HslVU and Lon in bacteria and their homologues in mitochondria and chloroplasts. With the exception of Lon, AAA+ enzymes (sometimes referred to as unfoldases or proteases) consist of regulatory (ATPase) and proteolytic subunits, while Lon is a single polypeptide containing both regulatory and proteolytic domains. ClpX and ClpA dock with ClpP to form ClpXP and ClpAP proteases, whereas HslU docks with HslV to form another protease, HslVU. ClpA and ClpX form hexamers, in contrast to ClpP which forms heptamers. HslU and HslV each form hexamers, although HslU heptamers have also been reported. The regulatory subunits ClpA, ClpX and HslU function as chaperones. Further details on ClpX may be found in Maillard et al., "ClpX(P) generates mechanical force to unfold and translocate its protein substrates," Cell 145:459-4669 (Apr. 29, 2011). As reported there, the ClpX motor shares is basic design with other AAA+ enzymes, including prokaryotic ClpA, ClpB, HsIu, FtsH or Lon. The AAA+ enzyme is also referred to as an "AAA+ molecular motor". Further description of the AAA+ superfamily is found in Ogura et al. "AAA+ superfamily ATPases" common structure-diverse function," Genes to Cells, 6:575-597 (2001). AS described there, the AAA+ family members associated with mitochondria are Bcs1p, Lon/Pim1p, ClpX and Hsp78.

The term "HsIU" is used herein to refer to ATP-dependent protease ATPase subunit HsIU, also called unfoldase HsIU. HsIU is a member of the Hsp100 and Clp family of ATPase. It can also form complex with HsIV to act as an unfoldase (See, Bochtler et al., "The structures of HsIU and the ATP-dependent protease HsIU-HsIV," Nature 403(6771): 800-805 (2000).

The term "Lon protease" is used herein to refer to a family of proteases found in archaea, bacteria and eukaryotes. Lon proteases are ATP-dependent serine peptidases belonging to the MEROPS peptidase family S16 (lon protease family, clan SF). In the eukaryotes the majority of the Lon proteases are located in the mitochondrial matrix. In yeast, the Lon protease PIM1 is located in the mitochondrial matrix. It is required for mitochondrial function, it is constitutively expressed but is increased after thermal stress, suggesting that PIM1 may play a role in the heat shock response.

The term "protein translocase" is used herein to mean a protein-binding polypeptide, such as a polypeptide which is able to control movement of a protein substrate, for example an enzyme, enzyme complex, or a part of an enzyme complex that operates on a protein substrate and moves it relative to the enzyme in a processive manner, i.e. as a function of enzymatic activity. The term "processive" is understood in the art to refer to a stepwise activity in which the enzyme "processes" the substrate in a number of steps. In the present case, the protein translocase generally processes the protein to be translocated in a sequential manner, that is, moving along the primary amino acid sequence. For convenience, a number of enzymes also commonly called "unfoldases" are included in this definition, in particular NTP driven unfoldases. Also specifically included in this definition is the AAA+ enzyme superfamily and the ClpX member of this superfamily.

Also included as examples of the general term "protein translocase" are proteases such as Lon protease and HsIU, which enzymes are either modified to eliminate the enzymatic cleavage activity of the enzyme or arranged so that cleavage occurs after the sequence is translocated through the nanopore.

Other exemplary protein translocases are related to ClpX, (which is also an unfoldase), e.g. ClpA, mitochondrial protein translocases TOM (translocase of the outer membrane) or other TOM and TIM proteins. The chosen protein translocase can also be any part of the mitochondrial protein translocase complex, such as the chaperones, TOM import receptor, TOM channel complex, and "motor" proteins.

The term "ClpX enzyme" of "ClpX" is used herein to refer to a member of the HSP (heat-shock protein) 100 family having the uniprot designation clpX. ClpX subunits associate to form a six-membered ring that is stabilised by binding of ATP or nonhydrolysable analogs of ATP. The N-terminal domain of ClpX is a C4-type zinc binding domain (ZBD) involved in substrate recognition. ZBD forms a very stable dimer that is essential for promoting the degradation of some typical ClpXP substrates such as lO and MuA. It is described further in Wawrzynow et al, "The ClpX heat-shock protein of *Escherichia coli*, the ATP-dependent substrate specificity component of the ClpP-ClpX protease, is a novel molecular chaperone," EMBO J. 1995 May 1; 14(9): 1867-1877, An amino acid sequence is also given at eclowiki.net under "clpX: gene products".

The term "non-denatured protein" is used herein used herein in its conventional sense, i.e. the protein is in its native secondary and tertiary structure, with any native cysteine bonds, hydrogen bonding and multimeric form essentially intact. This is contrasted with a denatured protein, which usually are insoluble and aggregated.

The term "negatively charged amino acids" is used herein in its conventional sense, i.e. meaning proteins that have surfaces rich with negatively charged amino acids like glutamate and aspartate.

General Method and Apparatus

Translocation of proteins through a nanopore (sensor) offers a number of possible applications, including sequencing, structure/fold analysis, purification/separation, intracellular protein delivery, and insight into the mechanics of enzymes driving the translocating polypeptide. Unlike nucleic acids, proteins are generally not uniformly charged (making it difficult to drive translocation via an applied voltage) and fold into complex, large, and stable structures that cannot transverse a nanopore's aperture. To address these issues, unfolding and translocation of natively folded proteins through a protein nanopore may be accomplished via a variety of enzymes, exemplified by the *E. coli* proteasome-like complex ClpA/X(P) (or homologous ClpA/X(P) proteins from a different organism).

The present methods and device may be used to measure one or more characteristics of the protein being translocated.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

The signal measurement is typically indicative of the identity of the protein or the amino acids in the protein. The signal can therefore be used to characterize, such as sequence, the protein as discussed above.

1. Enzymes Used for Translocation

E. coli ClpX is exemplified in the present device; it was selected for initial work because it generates sufficient mechanical force (>20 pN)[11] to denature stable protein folds, and because it translocates along proteins at a suitable rate for primary sequence analysis by nanopore sensors (up to 80 amino acids per second). ClpA/X acts as a gate that allows for tagged proteins to enter into the inner lumen of the ClpP protease complex for subsequent degradation.

This ATP-dependent unfoldase/translocase activity of the hexameric protein complex, ClpA/X, was employed to unfold and thread proteins through a nanopore.

As referred to above, a variety of alternative enzymes may serve the function of the protein translocase in the present method and device. CLpX may be prepared as described in Martin et al. "Rebuilt AAA+ Motors reveal operating principles for ATP-fuelled machines," Nature 437:1115-1120 (2005).

The repertoire of cellular functions involving AAA+ ATPases is diverse. A subset of AAA+ proteins is not active as ATPases and some do not even bind ATP. It seems however, that these proteins form complexes with other family members which do serve as ATPases. However, the ATPase subunits or domains of all known ATP-dependent proteases belong to the AAA+ family.

One example of a suitable AAA+ enzyme is Clp/Hsp100 ATPases. Clp/Hsp100 ATPases are responsible for selecting protein targets. For example, the two different bacterial ATPases ClpX and ClpA impart distinct substrate preferences to the ClpP peptidase. The ssrA degradation sequence, an 11-residue peptide that is appended to polypeptides stalled on the ribosome, is recognized by both ClpX and ClpA. Mutational analysis of the ssrA sequence revealed that this same tag is recognized by the two unfolding enzymes via different residues, further confirming the distinct binding preferences of each ATPase.

Using the energy from ATP-hydrolysis, Clp/Hsp100 enzymes actively direct structural changes in their substrates. These ATP-driven structural changes result in two distinct biological outcomes for the protein substrates: degradation or remodeling. ClpA, based on its ability to degrade casein, was the first prokaryotic Clp/Hsp100 protein functionally identified. Accordingly, the degradation pathway for the Clp/Hsp100 proteins is the better characterized of the two processes. During Clp/Hsp100-facilitated protein degradation, first, the Clp/Hsp100 component recognizes and selects a target protein. The enzyme binds to a short peptide sequence (e.g., the ssrA degradation tag) usually located near either the C or N terminus of the substrate. Then, in a reaction that requires multiple cycles of ATP-hydrolysis, the enzyme unfolds and directionally translocates the target substrate to the peptidase chamber where it is degraded.

The protein translocases used in the present methods and devices can also be any corresponding mitochondrial protein translocase. These may be translocases TOM or TIM from human or eukaryotic cells, such as TOMM20 (translocase of outer mitochondrial membrane 20 homolog), TOMM22 (mitochondrial import receptor subunit 22 homolog), TOMM40 (translocase of outer mitochondrial membrane 40 homolog), TOM7 (translocase of mitochondrial outer membrane 7), TOMM7 (translocase of outer mitochondrial membrane 7 homolog), TIMM8A (translocase of inner mitochondrial membrane 8 homolog A), TIMM50 (translocase of inner mitochondrial membrane 50 homolog). For example, TOMM40 is embedded into outer membranes of mitochondria and is required for the movement of proteins into mitochondria. More, precisely, TOMM40 is the channel-forming subunit of a translocase of the mitochondrial outer membrane (TOM) that is essential for protein transport into mitochondria Another alternative protein translocase is SecB (chaperone protein), SecA (ATPase), SecY (internal membrane complex in prokaryotes), SecE (interal membrane complex in prokaryotes), SecG (internal membrane complex in prokaryotes) or Sec61 (internal membrane complex in eukaryotes), SecD (membrane protein), and SecF (membrane protein).

Another alternative protein translocase is Type III Secretion System (TTS) Translocase, such as HrcN and any of the 20 subunits of the TTS translocases, or Sec-independent periplasmic protein translocase TatC.

Other alternative protein translocases are chaperones. These are proteins that assist the non-covalent folding or unfolding and the assembly or disassembly of other macromolecular structures, but do not occur in these structures when the structures are performing their normal biological functions having completed the processes of folding and/or assembly. Many chaperones are heat shock proteins, that is, proteins expressed in response to elevated temperatures or other cellular stresses. Hsp 70, as is known, refers to 70-kDa heat shock proteins (Hsp70s), such as DnaK, HscA (Hsc66), and HscC (Hsc62) in prokaryotes, and Hsc70, Hsp70, BiP or Grp78 (binding immunoglobulin protein), mtHsp70 or Grp75 in eukaryotic organisms, and human Hsp70 proteins, such as Hsp70, Hsp70-2, Hsp70-4, Hsp70-4L, Hsp70-5, Hsp70-6, Hsp70-7, Hsp70-8, Hsp70-9, Hsp70-12a, Hsp70-14. Hsp70 proteins are central components of the cellular network of molecular chaperones and folding catalysts. Hsp70s assist a wide range of folding processes, including the folding and assembly of newly synthesized proteins, refolding of misfolded and aggregated proteins, membrane translocation of organellar and secretory proteins, and control of the activity of regulatory protein. ATP binding and hydrolysis are essential in vitro and in vivo for the chaperone activity of Hsp70 proteins.

Hsp70 chaperone families are recognized as most common remodeling enzyme together with Hsp60 chaperone families. Hsp70s and Hsp60s prevent off-pathway interactions during protein folding by providing an isolated environment for the folding protein. In contrast, the Clp/Hsp100 unfolding enzymes actively direct the structural changes in their substrates. Clp/Hsp100s act on folded and assembled complexes, as well as improperly folded and aggregated proteins.

HSP90 aids the delivery of the mitochondrial preprotein to the TOM complex in an ATP-dependent process.

Hsp100 (Clp family in *E. coli*) proteins have been studied in vivo and in vitro for their ability to target and unfold tagged and misfolded proteins. Proteins in the Hsp100/Clp family form large hexameric structures with unfoldase activity in the presence of ATP. These proteins are thought to function as chaperones by processively threading client proteins through a small 20 Å (2 nm) pore, thereby giving each client protein a second chance to fold. Some of these Hsp100 chaperones, like ClpA and ClpX, associate with the double-ringed tetradecameric serine protease ClpP; instead of catalyzing the refolding of client proteins, these complexes are responsible for the targeted destruction of tagged and misfolded proteins.

Hsp104, the Hsp100 of *Saccharomyces cerevisiae*, is essential for the propagation of many yeast prions. Deletion of the HSP104 gene results in cells that are unable to propagate certain prions.

2. Enzymes Used for Transport May be Coupled to the Nanopore, Free in Solution on One Side, and/or Present on Both Sides of the Nanopore Coupling of ClpA/X to the nanopore may be achieved in different ways: 1) via an engineered alpha-hemolysin/ClpP fusion protein pore that will assemble to form an active heptameric protein nanopore covalently fused at its N-terminal cap domain to the ClpA/X-binding domain of the ClpP heptamer complex. Fusion of the ClpA/X-binding domain of ClpP to the top of the nanopore will enable ClpA/X to assemble in solution, attach to the ClpP domain, and function on the top of nanopore. 2) ClpA/X complexes will be placed in solution on the trans-side of the nanopore, and the substrate protein (dissolved in opposite (*cis*) side of the nanopore solution) N/C-termini will be forced to thread through the nanopore (for example, voltage-driven by engineering a few charged amino acids into the protein terminus, such as 5-10 Asp, Lys or Arg residues) where the ClpA/X complex will capture this tagged polypeptide tail, and begin mechanically pulling/translocating the substrate down through the nanopore. Thus, both strategies will utilize native ClpA/X binding, unfolding, and translocation activity of tagged proteins to control the movement of proteins through a nanopore sensor for subsequent analysis.

In the working example, the protein translocase is added in solution to the trans side of the chamber; it serves to unfold the protein to be translocated by pulling it through the nanopore, which is too narrow to permit passage of the folded protein. The same or a different protein translocase may be located on the *cis* side of the nanopore for unfolding the protein.

FIG. 10 illustrates a fusion protein comprising the α-hemolysin pore protein subunits fused to subunits of a ClpP protein. The ClpA/X protein translocase can then non-covalently "dock" onto the ClpP subunits. In this embodiment the protein translocase is on the *cis* side of, and fused to, the nanopore.

3. Nanopore Sensing

The method of sensing in the present method and device may involve measuring one, two, three, four or five or more characteristics of the protein. The one or more characteristics are preferably selected from (i) the length of the protein, (ii) the identity of the protein, (iii) the sequence of the protein, (iv) the secondary structure of the protein and (v) whether or not the protein is modified. Any combination of (i) to (v) may be measured in accordance with the invention.

For characteristic (i), the length of the protein may be measured using the number of interactions between the protein and the pore.

For characteristic (ii), the identity of the protein may be measured in a number of ways. The identity of the protein may be measured in conjunction with measurement of the sequence of the protein or without measurement of the sequence of the protein. The former is straightforward; the protein is sequenced and thereby identified. The latter may be done in several ways. For instance, the presence of a particular motif in the protein may be measured (without measuring the remaining sequence of the protein). Alternatively, the measurement of a particular electrical and/or optical signal in the method may identify the protein as coming from a particular source.

For characteristic (iii), the sequence of the protein can be determined as described herein. The sequence may be determined on an individual amino acid residue-by-residue basis, or may be read in blocks of amino acids, which may be mapped to known protein sequences, in a manner analogous to re-sequencing of DNA. Thus the method need not resolve each individual amino acid, but rather one could just resolve "words" or blocks/chunks of amino acids (e.g. 2 to 10 aa) that would still enable identification of the protein/polypeptide sequence.

For characteristic (iv), the secondary structure may be measured in a variety of ways. For instance, if the method involves an electrical measurement, the secondary structure may be measured using a change in dwell time or a change in current flowing through the pore.

For characteristic (v), the presence or absence of any modification may be measured. The method preferably comprises determining whether or not the protein is modified by methylation phosphorylation, oxidation, by damage (e.g. misfolding or covalent modification of an amino acid), by glycosylation or with one or more labels, tags or spacers. Specific modifications will result in specific interactions with the nanopore which can be measured using the methods described below.

4. Detection of Sequence-Related Current States

As discussed below, the present methods and device can extract protein sequence information from the protein being translocated by analysis of the ionic current measured through the nanopore. This is partly dependent on the use of sensitive electronics such as a patch clamp amplifier, a finite state machine, and signal processing such as weighted averaging, all described below. In addition, the present methods involve analysis of various current states that have now been found to be associated with the transit of the protein through the nanopore and the concomitant current blockage, unblockage or modulation. As described below, the signal detected by protein traversal will enter a so-called "ramping state" which is characteristic of binding of the protein to the nanopore, then a series of separate amplitude transitions as the protein translocates through the nanopore, followed by an open state equivalent to current through the pore prior to translocation. In summary, using the exemplified experimental setup, one can observe distinct states (see FIG. 2) of (i) open channel current, prior to translocation—about 30-35 pA, or 32-36 pA;

(ii) decrease to about 10-15 (e.g. about 13-15) pA upon capture of the protein to be translocated (i.e. the protein blocks the nanopore opening;

(iii) decrease below 10 pA and various amplitude changes (including a "ramping" effect discussed below), as the protein unfolds and translocates through the nanopore; and (iv) return to open channel state.

Importantly, state (iii) (FIG. 2B) presents a current pattern that can be correlated to protein structure. As described below, the artificial linkers used in the examples showed different current amplitudes and duration. When analyzing a protein to determine an unknown feature such as sequence, one may correlate observed changes in amplitude and RMS noise to the amino acid-dependent features of the translocated protein. This includes but is not limited to tertiary and secondary structures, amino acid sequence and post-translational modifications.

5. Exemplary Applications (1) A nanopore device can be used to monitor the turnover of enzymes such as proteases, kinases, and phosphatases, which have important applications in cell proliferation.

(2) A nanopore device can function as a biosensor to monitor the interaction between soluble substances such as enzyme substrates or signaling molecules. Examples include blood components such as glucose, uric acid and urea, hormones such as steroids and cytokines, and pharmaceutical agents that exert their function by binding to receptor molecules.

(3) A nanopore device can monitor in real time the function of important biological structures such as ribosomes, and perform this operation with a single functional unit.

The present methods and devices may be used to detect and quantify altered protein expression, absence/presence versus excess, expression of proteins or to monitor protein levels during therapeutic intervention. The amount of protein in a given sample may be estimated using an array of nanopore devices according to the present invention. Polypeptides or proteins to be translocated can also be utilized as markers of treatment efficacy against the diseases noted above and other brain disorders, conditions, and diseases over a period ranging from several days to months. Qualitative or quantitative methods for this comparison are well known in the art.

6. Manufacture of Single Channel Thin Film Devices

Single-channel thin film devices and methods for using the same are provided. The subject devices typically comprise a mixed-signal semiconductor wafer, at least one electrochemical layer, the electrochemical layer comprising a semiconductor material, such as silicon dioxide or the like, wherein the semiconductor material further comprises a surface modifier, such as a hydrocarbon, wherein the electrochemical layer defines a plurality of orifices, the orifices comprising a chamber and a neck and wherein the chamber of the orifices co-localize with a first metal composition of the mixed-signal semiconductor wafer, wherein a portion of the orifice is plugged with a second metal, for example, silver, wherein the second metal is in electronic communication with the first metal, and wherein the orifice further comprises a thin film, such as a phospholipid bilayer, the thin film forming a solvent-impermeable seal at the neck of the orifice, the thin film further comprising a pore, and wherein the orifice encloses an aqueous phase and a gas phase.

Biological nanopores have utility in detection of polypeptides but, due to the low current used (approximately in the tens of picoamps). Manufacturing arrays of biological nanopores that can operate independently of each other, such as used in the manufacture of very large arrays of integrated circuits, allow a very large scale array of nanopores to perform millions of biochemical reactions and analyses in a single second.

The array elements may be manufactured in a step-wise parallel manner, similar to the manufacture of transistors on integrated circuits. All, or most, of the similar layers of each array element are created in a sequence of single process steps that simultaneously take place on all, or most, of the array elements.

There appears to be no simple way to synchronize the activities of separate molecules of biological reagents, so each element in the array should be able to act independently of the other elements. This may be accomplished by including a digital logic circuit with each single biological nanopore that implements a finite state machine that controls and senses the biochemical state of the complex off single (or multiple) molecules associated with the biological nanopore. The finite state machine allows low latency control of the complex of molecules associated with the biological nanopore and at the same time can store information gathered for retrieval at another time.

In order that each of the biological nanopore elements in an array may be in communication with one another using a minimum number of wired connections, a serial interface and addressable logic can be used to multiplex the large amount of data entering and exiting the array.

Not all of the array elements may have a thin film or bilayer across their respective orifice. The capacitance of the membrane present in the nanopore as measured by the finite state machine can be used to detect the presence of non-functional array elements. If it is subsequently determined that a proportion of array elements lack a thin film or bilayer is greater when compared with a proportion that is preferred, then the step of overlaying the membrane such as TEFLON film and lipid coat can be repeated.

An electrode, for example a grounded macroscopic AgCl electrode, may be placed in contact with second solution. When membranes such as bilayers are positioned in place across all the functionable orifices, no ion current will flow from second solution to first solution. A predetermined amount of pore molecule or channel molecule, such as for example, a-hemolysin toxin or MspA, is added to second solution. The concentration of pore molecule or channel molecule is sufficient to form a single channel in any of the thin films or bilayers in approximately, for example, fifteen minutes. The time to form such channels can be for example, between one-half minute and one hour, for example, about one-half minute, one minute, two minutes, three minutes, four minutes, five minutes, seven minutes, ten minutes, fifteen minutes, twenty minutes, twenty five minutes, thirty minutes, thirty five minutes, forty minutes, forty five minutes, fifty minutes, fifty five minutes, sixty minutes, or any time therebetween. The time for formation can be altered by an operator by several factors or parameters, for example, increasing or decreasing the ambient or incubation temperature, increasing or decreasing the concentration of salt in second solution or first solution, placing a potential difference between the first solution and the second solution, or other methods know to those of skill in the art. The finite state machine can detect and/or sense formation of a single channel in its corresponding bilayer by reacting to the flow of current (ions) through the circuit, the circuit comprising the macroscopic electrode, the second solution, the single nanopore or channel molecule, first solution, and the metal electrode for any given array element.

Formation of biological channels is a stochastic process. Once a single channel has formed in a given array element bilayer, it is preferred that the chance that a second channel so forming therein is reduced or preferably, eliminated. The probability of second channel insertion can be modulated with applied potential, that is, potential difference, across the bilayer. Upon sensing a single channel, a finite state machine may adjust the potential on the metal electrode to decrease the possibility of second channel insertion into the same bilayer.

Despite the precautions taken in the previous step(s) a second channel may form in a given bilayer. The finite state machine can detect the formation of the second channel. A pulse of precisely controlled low pressure can force one out of two channels allowing a single channel to remain embedded in the bilayer.

In the course of using the biological nanopore for biochemical actuation and detection, the pore may become permanently obstructed. A finite state machine can detect and sense this obstructed state and can remove the blocked channel from the bilayer by inactivating the heating element thereby applying suction (reduced pressure) upon the bilayer.

In an alternative embodiment, each array element may comprise a gold electrode surrounding the orifice. This gold electrode may serve to activate chemical reagents using reduction or oxidation reactions and that can act specifically at the location of a specific orifice.

The finite state machine can be created for example using state-of-the-art commercially available 65 nm process technology, for example from Taiwan Semiconductor Manufacturing Company, Taiwan). A 600×600 array of nanopores can perform 360,000 biochemical reaction and detection/sensing steps at a rate of 1000 Hz. This may enable sequencing of polynucleotides, for example, to proceed at a rate of 360 million baser per second per 1 cm×1 cm die cut from the semiconductor wafer.

Exemplary means for applying an electric field between the cis- and trans-chambers are, for example, electrodes comprising an immersed anode and an immersed cathode, that are connected to a voltage source. Such electrodes can be made from, for example silver chloride, or any other compound having similar physical and/or chemical properties.

Equipment

A patch-clamp amplifier, Molecular Devices AxoPatch 200B, regulates the applied voltage and measures the ionic current through the channel. The data are recorded using the Molecular Devices Digidata 1440A digitizer, sampled at 50 kHz and low-pass filtered at 5 kHz with a four-pole Bessel filter.

Control Logic: Hardware and Software

The voltage control logic is programmed using a finite state machine (FSM) within the LabVIEW 8 software. The FSM logic is implemented on a field-programmable gate array (FPGA) hardware system, National Instruments PCI-7831R. An FPGA is a reconfigurable hardware platform that permits fast measurement and voltage reaction times (1 μsec output sample time). An FSM is a logic construct in which program execution is broken up into a series of individual states. Each state has a command associated with it, and transitions between states are a function of system measurements. Measurements of the pore current are processed and passed to the FSM as inputs. Changes in the FSM control logic are made as necessary, without the need to re-compile and re-route the design to run on the FPGA. This achieves a balance between speed and flexibility, by enabling the system to react to events on the order of a microsecond, while also allowing for the control logic to be reconfigured as necessary between experiments.

Moving Average Filter

Every 5.3 μsec, the FPGA samples the ionic current and computes a windowed mean amplitude, using a window size of 0.75 msec. If the mean enters a chosen threshold range, the FPGA detects entry and continues to monitor the mean, re-checking the threshold every 0.2 msec. If the mean remains within the threshold range for four consecutive checks, the FSM logic diagnoses the blockade as an event type known to be consistent with the chosen threshold.

In the absence of a change in voltage, the expected time delay between the start of an event and diagnosis of an event is 1.35 msec; 0.75 msec for the windowed mean to first enter the threshold, and 0.6 msec for three more confirmed tests. In practice, the diagnosis time ranges from 1.1 to 2.5 msec. The mean filter was implemented in our invention's initial demonstration Exponentially-Weighted Moving Average Filter To improve the FSM's robustness to false detections of terminal steps, an exponentially-weighted moving average (EWMA) filter may be used to replace the mean filter. The EWMA filter represents a digital implementation of an analog RC filter commonly used for signal smoothing in electrical engineering applications. The filter calculates a moving average that places exponentially less significance on past samples and allows the filtered signal to better track the real signal. EWMA filtering also performs signal smoothing more efficiently than a simple moving average due to its recursive implementation:

$$i(t)=(1-a)i(t)+ai(t-1), \quad (1)$$

where i and i are unfiltered and filtered current signals, respectively, and t is the sample number. Filtering the data from the terminal step detection experiments offline, with α=0.9, showed a substantial improvement in robustness to false positives over the mean filter. As with the mean filter, four consecutive threshold tests will be used for event diagnosis, waiting 0.2 msec between threshold tests.

In the absence of a change in voltage, the expected time delay between the start of an event and diagnosis of an event is 0.7 msec; 0.1 msec for the EWMA to first enter the threshold, and 0.6 msec for three more confirmed tests. More rigorous evaluation of EWMA detection times will be part of our ongoing work.

Voltage Control Using FSM/FPGA

A patch-clamp amplifier, Molecular Devices AxoPatch 200B, regulates the applied voltage and measures the ionic current through the channel. The data are recorded using the Molecular Devices Digidata 1440A digitizer, sampled at 50 kHz and low-pass filtered at 5 kHz with a four-pole Bessel filter.

The voltage control logic is programmed using a FSM within the LabVIEW 8 software. The FSM logic is implemented on a field-programmable gate array (FPGA) hardware system, National Instruments PCI-7831R. An FPGA is a reconfigurable hardware platform that permits fast measurement and voltage reaction times (1 μsec output sample time). An FSM is a logic construct where program execution is broken up into a series of individual states. Each state has a command associated with it, and transitions between states are a function of system measurements. Measurements of the pore current are processed and passed to the FSM as inputs. Changes in the FSM control logic are made as necessary, without the need to re-compile and reroute the design to run on the FPGA. This achieves a balance between speed and flexibility, by enabling the system to react to events on the order of a microsecond, while also allowing for the control logic to be reconfigured as necessary between experiments.

Example 1

Construction of a Nanopore Device for Monitoring Protein Translocation

The nanopore device of this example is diagrammed in FIG. 1A, which shows diagrammatic drawing of a nanopore sensor with a single α-HL pore embedded in a lipid bilayer separating two Teflon® PTFE polymer wells each containing 100 µl of 0.2 M KCl solution (30° C.). Voltage is applied between the wells (trans side+180 mV), causing ionic current flow through the channel. Current diminishes in the presence of a captured protein molecule.

Briefly, for each experiment a single α-HL nanopore was inserted into a 30 µm diameter lipid bilayer that separates two wells (termed cis and trans) that each contained 100 µl of PD buffer (pH7.6). A covalently-linked trimer of an N-terminal truncated ClpX variant (ClpX-ΔN$_3$) was used for all ClpX nanopore experiments. The ClpX-ΔN$_3$ BLR expression strain was obtained from Andreas Martin (UC Berkeley). ClpX protein expression was induced at an OD 600 of ~1 by addition of 0.5 mM IPTG, and incubated at 23° C. with shaking for 3-4 hours. Cultures were pelleted, resuspended in lysis buffer (50 mM NaH2PO4 pH 8, 300 mM NaCl. 100 mM KCl, 20 mM imidazole, 10% glycerol, 10 mM BME) and lysed via vortexing with glass beads. After centrifugation and filtration of the lysate, the protein was purified on a Ni2+—NTA affinity column (Thermo) and an Uno-Q anion exchange column (Bio-Rad).

Both cis compartment and trans compartment are filled with 100 µl of a 200 mM KCl buffer optimized for ClpX function. This buffer was supplemented with 5 mM ATP as indicated. A patch-clamp amplifier (Axopatch 200B, Molecular Devices) applied a constant 180 mV potential between two Ag/AgCl electrodes (trans side+) and recorded ionic current through the nanopore as a function of time. Substrate proteins were added to the cis solution at ~1 µM final concentration, while ~100 nM ClpX was present in the trans solution.

A constant 180 mV potential was applied across the bilayer and ionic current was measured through the nanopore between Ag/AgCl electrodes in series with an integrating patch clamp amplifier (Axopatch 200B, Molecular Devices) in voltage clamp mode. Data were recorded using an analog-to-digital converter (Digidata 1440A, Molecular Devices) at 100 kHz bandwidth in whole-cell configuration (β=1) then filtered at 5 kHz using an analog low-pass Bessel filter. Experimental conditions were prepared by the daily preparation of PD/ATP 5 mM and PD/ATP 4 mM. ClpX was diluted 1:10 in PD/ATP 5 mM for a final concentration of 30-100 nM ClpX in 4.5 mM ATP final. ClpX solution was used to fill the entire system before isolation of a single α-HL nanopore. Upon insertion, the cis well was perfused with ~6 mL PD/ATP 4 mM. Experiments were conducted at 30° C. with 1-2 µM substrate added to the cis well. Protein substrate capture events were ejected with reserve polarity due to pore clogs or after a predetermined duration. Voltage-induced translocations were frequently ejected to prevent clogging and to increase the efficiency of data collection. A single nanopore experiment is defined as the time during which ionic current data were acquired from one α-HL nanopore in an intact bilayer before termination by bilayer rupture, loss of channel conductance or completion of a preset number of translocation events.

Example 2

Engineering Protein S1, S2-35 and S2-148 for Translocation

These proteins are schematically illustrated in FIG. 1C, which shows (i) S1, a protein bearing a single N-terminal Smt3-domain coupled to a 65-amino-acid-long charged flexible segment capped at its carboxy-terminus with the 11 amino acid ClpX-targeting domain (ssrA tag); (ii) S2-35, similar to S1 but appended at its N-terminus by a 35 amino acid linker and a second Smt3 domain; (iii) S2-148, identical to S2-35 except for an extended 148 amino acid linker between the Smt3 domains.

For our initial experiments, we used a modified version of the ubiquitin-like protein Smt3. Smt3 is comprised of ~100 amino acids arranged into four β-strands and a single α-helix. We further engineer Smt3 into S1. To construct substrate protein S1, DNA encoding the 76 amino acid tail (GGSSGGSGGSGSSGDGGSSGGSGGSGSSGDGGSSGG SGGDGSSGDGGSDGDSDGSDGD GDSDGDDAANDE-NYALAA) (SEQ ID NO: 1) was constructed by polymerase chain reaction (PCR) and cloned into pET-SUMO vector (Invitrogen) at the T/A-cloning site, fusing the tail sequence onto the Smt3 sequence 3' end.

The 76 amino acid tail contained about 10 negatively charged residues and the 11 amino acid Clpx binding domain ssrA.

To facilitate nanopore analysis, the engineered Smt3 protein, S1, was modified in two ways, 1) It was appended with a 65-amino-acid-long glycine/serine tail including 13 interspersed negatively charged aspartate residues (SEQ ID NO: 6). This unstructured polyanion was designed to promote capture and retention of S1 in the electric field across the nanopore. Based on its crystal structure[13], the Smt3 folded domain is predicted to sit on top of the α-HL vestibule (FIG. 1B). 2) The appended polyanion was capped at its C-terminus with the ssrA tag, an 11 amino acid ClpX-targeting motif[14]. This ssrA peptide tag allowed ClpX to specifically bind to the C-terminus of the protein when it threaded through the pore into the trans compartment.

S2-35 (SEQ ID NO:5) was constructed by PCR-based addition of DNA encoding the 35 amino acid linker (GGSGSGGSGSGGSGSQNEYRSGGSGSGGSGSGGSG) (SEQ ID NO: 2) to the 5' end of the S1 Smt-3 sequence. This linker-modified S1 gene was then cloned into pE-SUMO vector (LifeSensors) at the BsaI site, fusing the added linker and S1 sequence to the 3' end of the pE-SUMO Smt3 sequence.

DNA for the S2-148 (SEQ ID NO: 6) linker addition (GGSGSAGSGASGSSGSEGSGASGSAGSGSAGSRGS-GASGSAGSGSAGSGGAEAAKEAA KEAAKEAAKEAAKAGGSGSAGSAGSASSGSDGS-GASGSAGSGSAGSKGSGASGSAGSG SSGS) (SEQ ID NO:3) was constructed by PCR, and cloned into the S2-35 vector within the 35 amino acid linker region by the Gibson assembly method. These engineered proteins were expressed in BL21 (DE3)*. Expression was induced at ~0.6 OD 600 by addition of 0.5 mM IPTG, and incubated at 37° C. with shaking for 4-6 hours. Cultures were pelleted, resuspended in lysis buffer and lysed via vortexing with glass beads. After centrifugation and filtration of the lysate, the protein was purified on a Ni$^{2+}$-NTA affinity column (Thermo).

Example 3

Detection of Translocation of Protein S1

A representative ionic current trace for capture and translocation of protein S1 in the presence of ClpX and ATP is shown in FIG. 2A. FIG. 2A shows the ionic current traces during S1 translocation. (i) Open channel current through the α-HL nanopore under standard conditions (~34±2 pA, RMS noise 1.2±0.1 pA). (ii) Capture of the S1 substrate. Upon protein capture, the ionic current drops to ~14 pA (~0.7 pA RMS noise). (iii) ClpX-mediated ramping state.

Figure 5:
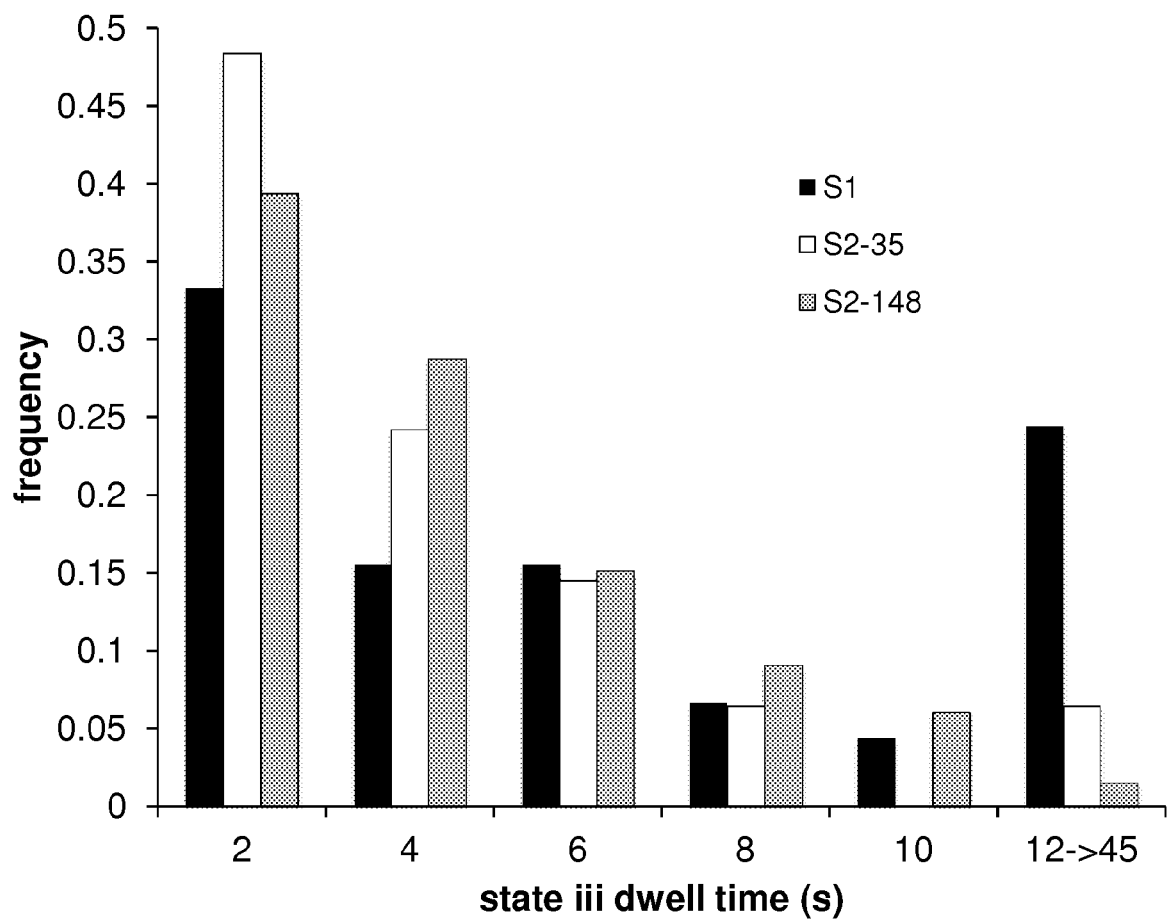
FIG. 5 is a frequency bar graph that demonstrates the comparison of ionic current state dwell times of ClpX-dependent (with ClpX present in the trans side) ramping state iii for the three model proteins. S1 n=45, S2-35 n=62, S2-148 n=66.

The ionic current decreases to below 10 pA and is characterized by one or more gradual amplitude transitions. This pattern is only observed in the presence of ClpX and ATP (trans compartment). (iv) Smt3 domain unfolding and translocation through the nanopore (~3.8 pA, 1.7 pA RMS noise). (v) Return to open channel current upon completion of substrate translocation to the trans compartment, From the open channel current of ~34±2 pA (FIG. 2A, i), S1 capture resulted in a current drop to ~14 pA (FIG. 2A, ii). This stable current lasted for tens of seconds and was observed in the presence or absence of ClpX and ATP added to the trans compartment (FIG. 4). This is consistent with the Smt3 structure held stationary atop the pore vestibule by electrical force acting on the charged polypeptide tail in the pore electric field. In the presence of ClpX and ATP, this initial current state was often followed by a progressive downward current ramp reaching an average of ~10 pA with a median duration of 4.3 seconds (FIG. 2A, iii and FIG. 5). This current ramp was observed with protein S1 a total of 45 times over ~5.5 hours of experimentation when ClpX and ATP were present; in contrast, the ramp was never observed following state ii when ClpX and ATP were absent from the trans solution over ~2.3 hours of experimentation. In a majority of events, the ClpX-dependent ramping state terminated with an abrupt ionic current decrease to about 3 pA (FIG. 2A, iv). The median duration for state iv was ~700 ms (FIG. 3A) before it ended in a rapid increase to open channel current (FIG. 2A, v).

Based on these data we hypothesized that ClpX served as a molecular machine that used chemical energy derived from ATP hydrolysis to pull the S1 protein through the nanopore. This process was intermittently assisted by electrical force as charged amino acids entered the pore electric field.

FIG. 2B illustrates the working model of ClpX-mediated translocation of S1. Cartoons i-v correspond to ionic current states i-v in panel a. Proposed steps in this process are diagrammed in FIG. 2B: i) open channel; ii) Protein S1 capture by the pore with the Stm3 segment perched above the vestibule with the slender, charged polypeptide tail segment extended into the pore lumen, and the ssrA tag in the trans compartment. In this ionic current state ClpX is not bound to S1 or, alternatively, has bound but is still distant from the pore; iii) ClpX advances along the S1 strand toward the trans-side orifice of the α-HL pore until it makes contact. Ionic current decreases due to proximity of ClpX to the pore; iv) under combined force exerted by ClpX and the pore electric field, the Stm3 structure atop the pore is sequentially denatured thus allowing the polypeptide to advance relative to the nanopore. In this state, the ionic current has decreased because larger amino acids (or Smt3 secondary structures) have entered the pore lumen. This ionic current state persists until the S1 protein is completely pulled into the trans compartment resulting in a return to the open channel current v.

Example 4

Detection of Translocation of Proteins S2-35 and S2-148

This model makes a testable prediction. If the observed current states are due to processive movement of polypeptide segments into the pore lumen driven in part by ClpX, then changing the protein primary structure should result in sequential changes in the ionic current pattern that are ClpX/ATP-dependent. In particular, addition of a second Smt3 domain should result in a second ramping state (FIG. 2A, iii) followed by a second state centered at 3 pA (FIG. 2A, iv). As a test, we fused a flexible glycine/serine-rich 35 amino acid linker to the N terminus of the S1 protein and capped this with a second Smt3 domain (protein S2-35, FIG. 1C, ii and Sequence List, S2-35). Thus, the single folded-component sequence of S1 (C-terminus>charged flexible tail>Smt3>N-terminus) is repeated twice in S2-35 (C-terminus>charged flexible tail>Smt3>flexible linker>Smt3>N-terminus).

When protein S2-35 was captured in the nanopore with ClpX/ATP present in the trans-compartment, an ionic current pattern with eight reproducible states was observed (FIG. 2C).

Figure 3:
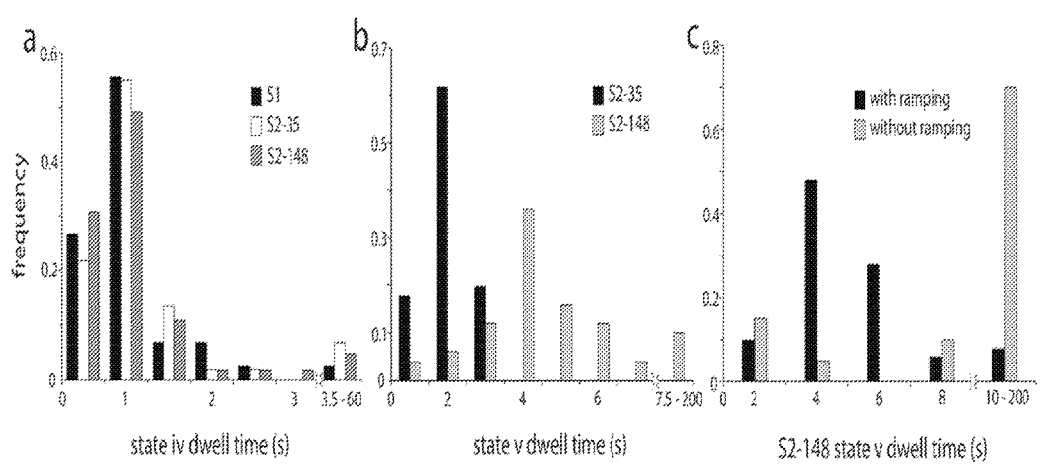
FIGS. 3A, 3B and 3C are bar graphs that shows the comparison of ionic current state dwell times for the three model proteins.
Figure 6:
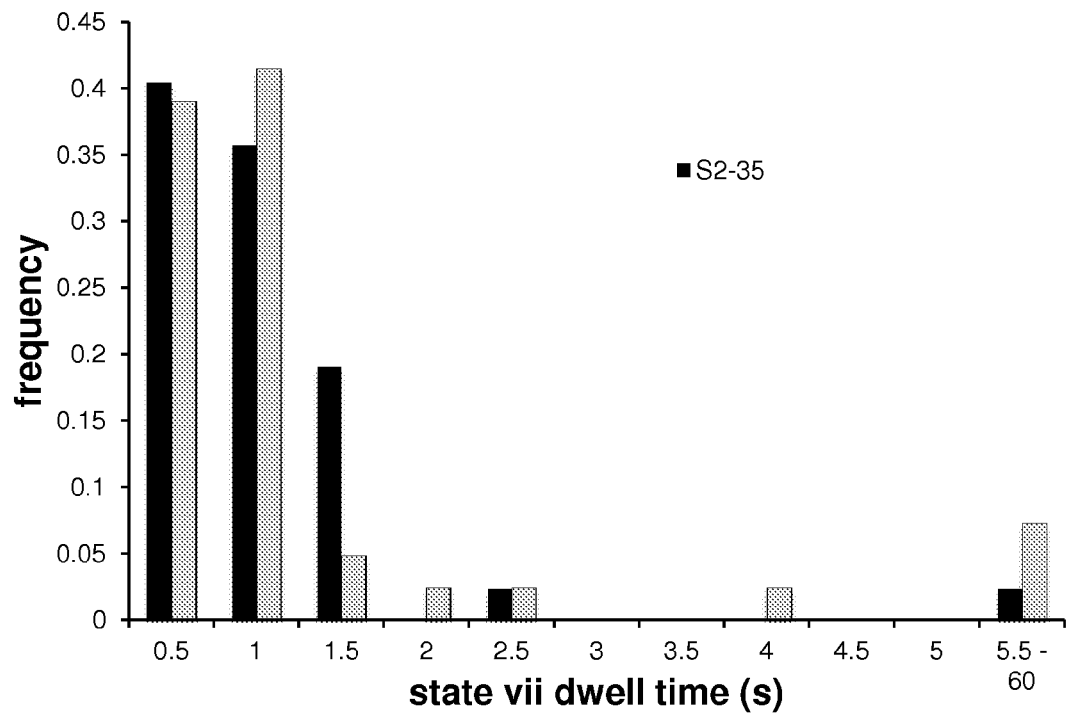
FIG. 6 is a frequency bar graph that shows the comparison of ionic current state dwell times of the putative second Smt3 domain translocation state vii of the S2-35 (n=42) and S2-148 (n=41) proteins in events that included ClpX-dependent ramping states iii and vi.
Figure 7:
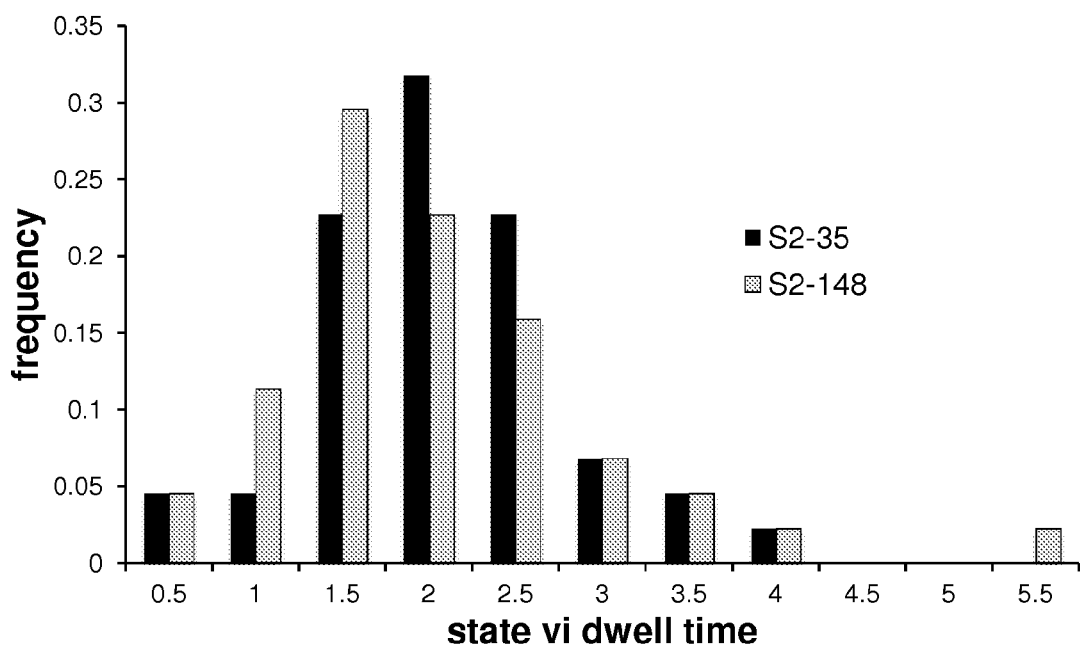
FIG. 7 is a frequency bar graph that shows the comparison of ionic current dwell times of ClpX-dependent ramping state vi of proteins S2-35 (n=44) and S2-148 (n=44).

FIG. 2C shows the ionic current traces during protein S2-35 translocation. Open channel current (state i) is not shown. States ii-iv are identical to states ii-iv in panel a. (v) Gradual increase in ionic current to about 10 pA. In our working model this corresponds to a transition from Smt3 domain translocation to linker region translocation. vi) A second putative ramping state that closes resembles ramping state iii. vii) A second putative Smt3 translocation state with ionic current properties that closely resemble state iv. viii) Return to open channel current. The first four states (FIG. 2C, i-iv) were identical to states i-iv caused by S1 translocation (compare FIGS. 2A and 2C). This similarity included ramping state iii that is diagnostic for ClpX engagement, and the Smt3-dependent state iv. However, beginning at state v, the S2-35 pattern diverged from the S1 pattern (compare FIGS. 2A and 2C). That is, following Smt3 state iv, a typical S2-35 ionic current trace did not proceed to the open channel current, but instead transitioned to a ~6 pA state with a median duration of 1.5 seconds (FIG. 2C, v and FIG. 3B). This was followed by a ~8.5 pA state (FIG. 2C, vi) that closely resembled ramping state iii, and a subsequent ionic current state that closely resembled the putative Smt3 translocation state iv (FIG. 2C, vii). In other words, consistent with our model, the putative ClpX-bound and Smt3-dependent states that were observed once during S1 events (FIG. 2A) were observed twice during S2-35 events (FIG. 2C). These analogous states for the two constructs shared nearly identical amplitudes, RMS noise values, and durations (FIG. 3A, FIG. 5, and FIG. 6).

This dependence of ionic current on protein structure is consistent with ClpX-driven protein translocation through the nanopore. As an additional test, we re-examined ionic current state v observed during S2-35 translocation. This state is consistent with movement of the 35 amino acid linker through the nanopore based on two observations: 1) its average ionic current is measurably higher than surrounding states (FIG. 2C) as expected for an amino acid sequence with few bulky side chains; and 2) in the time domain, ionic current state v occurs between Smt3-dependent ionic current states iv and vi as expected given its position along the S2-35 primary sequence (FIG. 1C, ii and related sequences).

If state v corresponds to translocation of the polypeptide linker under ClpX control, then changes in the length and composition of this linker should result in duration and current amplitude changes. For this test, we designed a third protein in which the S2-35 linker region was appended with an additional 113 amino acids, yielding a final construct consisting of two Smt3 domains separated by an extended 148 amino acid flexible linker (protein S2-148, FIG. 1C, iii, and sequences S2-148).

FIG. 2D shows the ionic current traces during protein S2-148 translocation. Ionic current states i-v and vi-viii were nearly identical to those states for S2-35 translocation (panel c). (v) In our working model, this ionic current state corresponds to translocation of the 148 amino acid linker. Its amplitude is ~3 pA higher than the S2-35 linker amplitude (~9 pA), and it has a median duration ~2.5 fold longer than the comparable S2-35 state v. Translocation events that included ramping state iii were observed 62 times for protein S2-35 (7.3 hours of experimentation), and 66 times for protein S2-148 (4.3 hours of experimentation), when ClpX and ATP were present. In the absence of ClpX/ATP, these ramping states were never observed for S2-35 (1.7 hours of experimentation), nor for S2-148 (1.2 hours of experimentation).

FIG. 3A shows state iv (putative Smt3 translocation state). These events included only those that manifest the ClpX-dependent ramping state iii. S1 n=45, S2-35 n=60, S2-148 n=65. FIG. 3B shows Comparison of linker region state v dwell times for the S2-35 and S2-148 proteins. Events included in these histograms manifest ramping state iii. S2-35 n=50, S2-148 n=50. FIG. 3C shows state v translocation dwell times for S2-148 translocation events. The black bars represent dwell times for events that included ramping state iii (ClpX-driven). The gray bars represent events that did not include the ramping state (not ClpX-driven). With ramping n=50, without ramping n=20.

As predicted, when this protein was captured in the nanopore under standard conditions in the presence of ClpX/ATP, eight reproducible states similar to S2-35 events were observed (FIG. 2d, FIG. 3A, FIGS. 5, 6, and 7).

Importantly, however, the S2-35 and S2-148 events differed significantly at state v (compare FIGS. 2c and 2d). That is, the S2-148 state v had a higher mean residual current than did S2-35 (~9 vs ~6 pA, respectively), and a median duration ~2.5 fold longer than that of S2-35 state v (FIG. 3B). The increased duration for S2-148 state v relative to S2-35 is expected as it should take ClpX longer to process the additional amino acids, while the increased current level is likely due to differences in linker amino acid composition between the two proteins (S2-35 linker: 51% Gly, 34% Ser, 15% other; S2-148 linker: 34% Gly, 32% Ser, 19% Ala, 15% other). However, we cannot exclude relative proximity of the proteins' Smt3 domains to the nanopore orifice that necessarily must differ due to the linker lengths.

Figure 8:
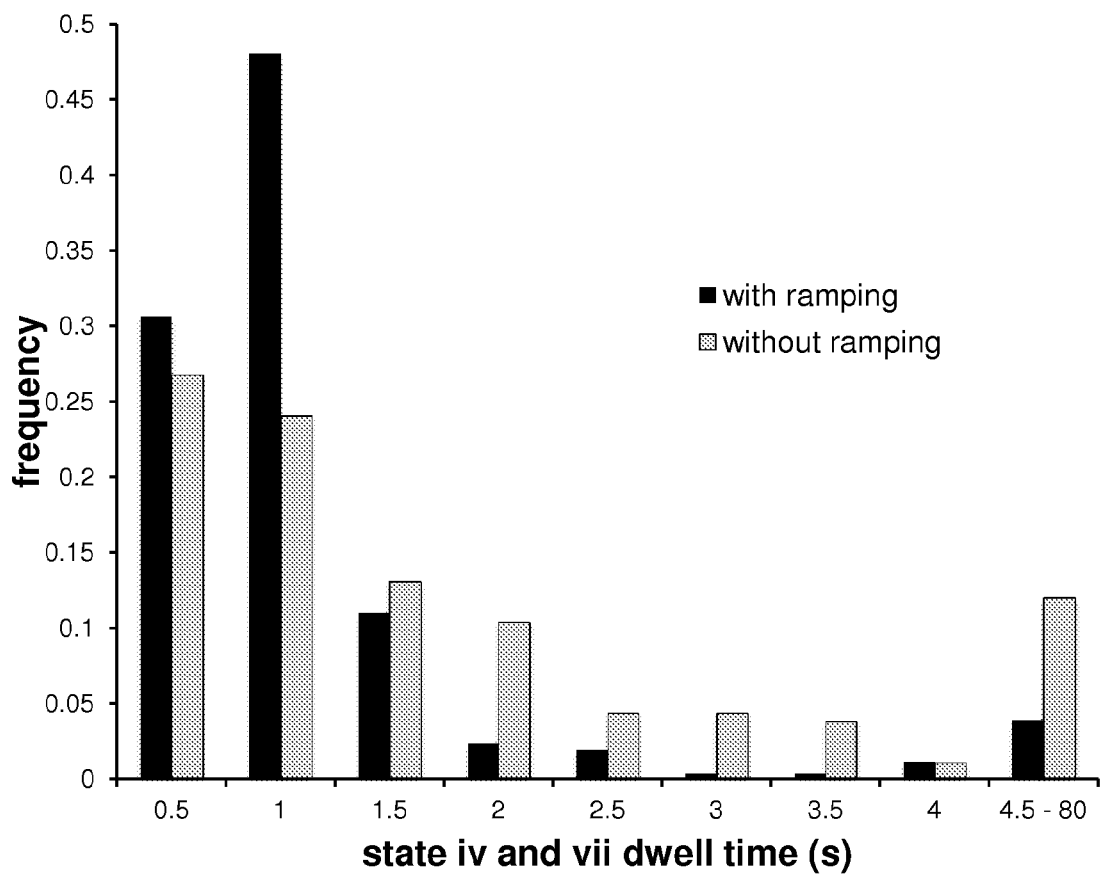
FIG. 8 is a frequency bar graph that shows the comparison of ionic current dwell times of the putative Smt3 domain translocation states iv and vii for the three model proteins. The black bars represent dwell times for events that included ramping state iii (ClpX-driven). The gray bars represent events that did not include the ramping state (not ClpX-driven). With ramping n=254, without ramping n=183.
Figure 9:
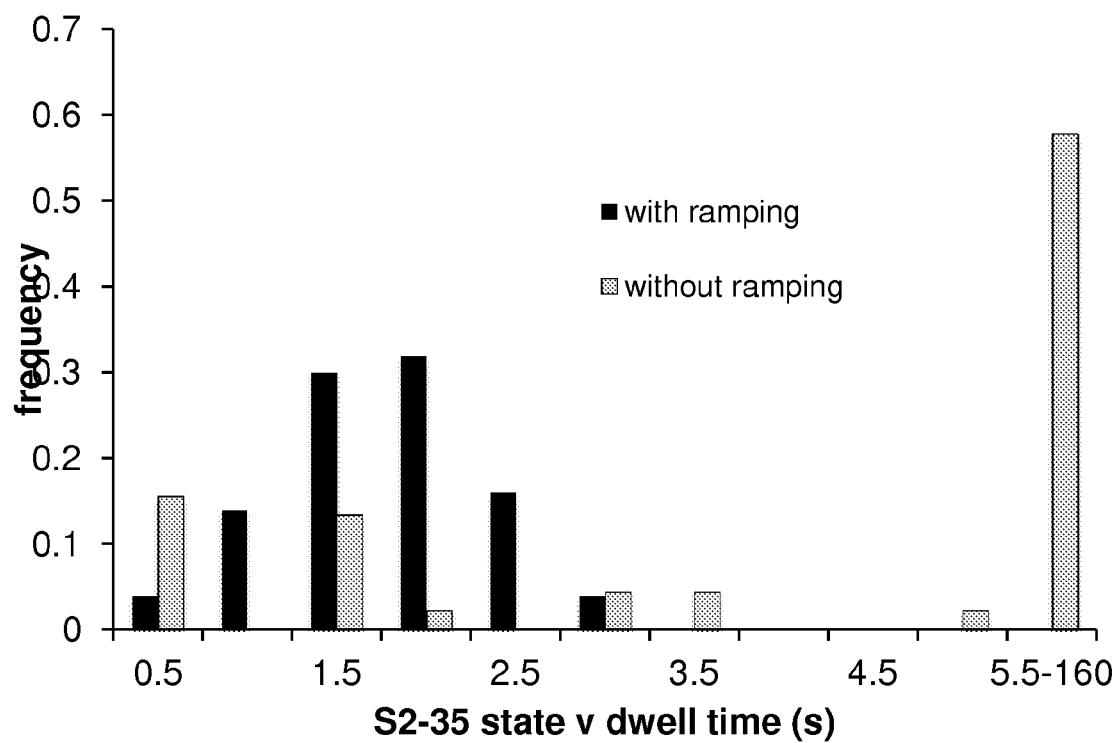
FIG. 9 is a frequency bar graph that shows state v dwell times for S2-35 translocation events. The black bars represent dwell times for events that included ramping state iii (ClpX-driven). The gray bars represent events that did not include the ramping state (not ClpX-driven). With ramping n=50, without ramping n=45.
Figure 10A:
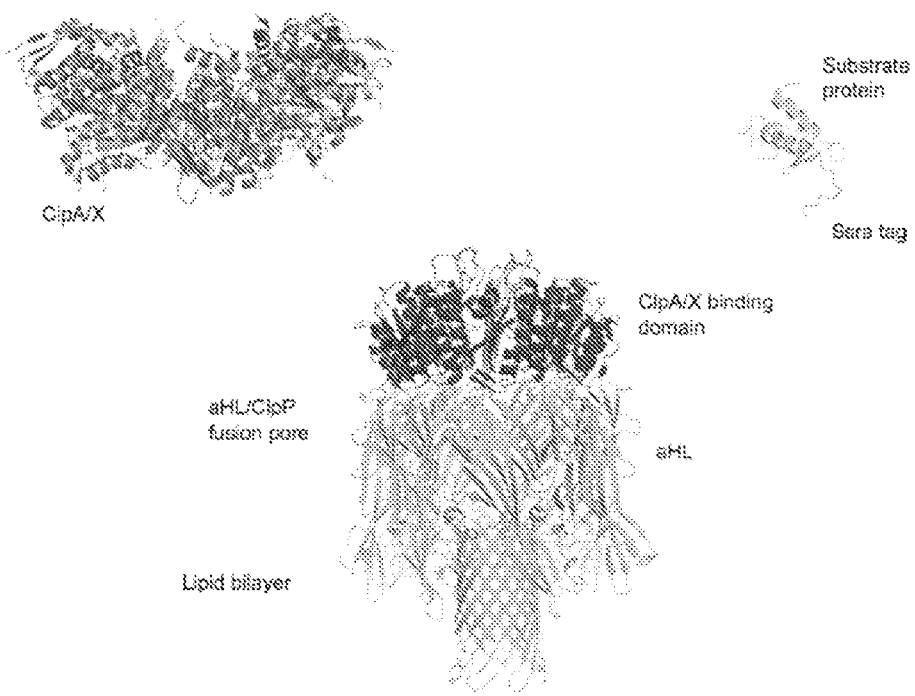
FIG. 10A is a diagrammatic representation that illustrates a fusion nanopore (ClpP/α-HL) embedded within a lipid membrane.
Figure 10B:
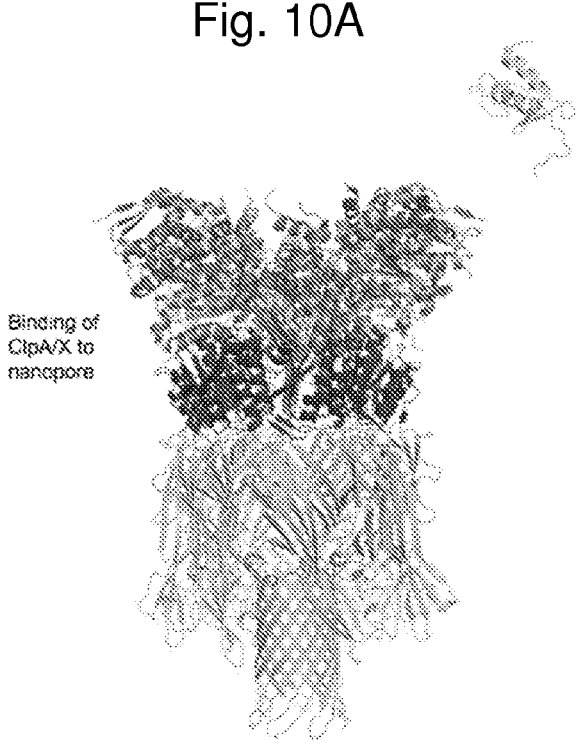
FIG. 10B illustrates ClpA/X binding to the ClpP domain of the fusion nanopore.
Figure 10C:
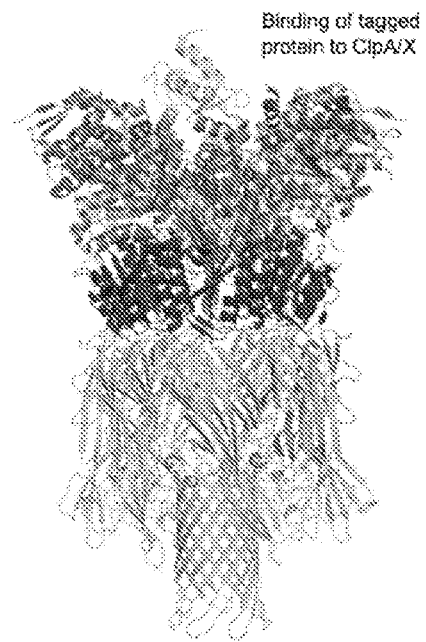
FIG. 10C illustrates substrate protein binding to ClpA/X.
Figure 10D:
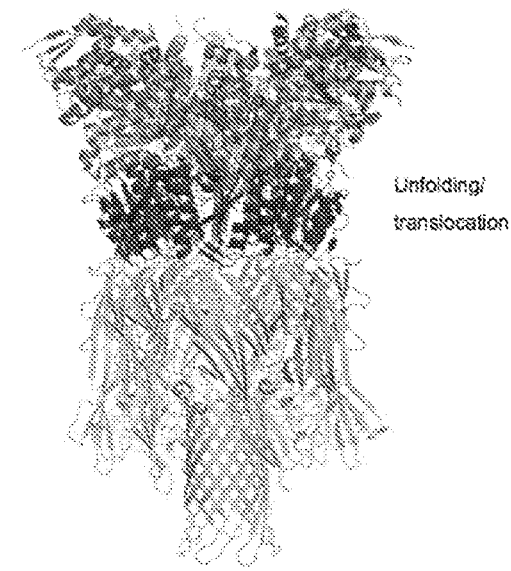
FIG. 10D and FIG. 10E illustrate substrate protein unfolds and translocates.
Figure 10E:
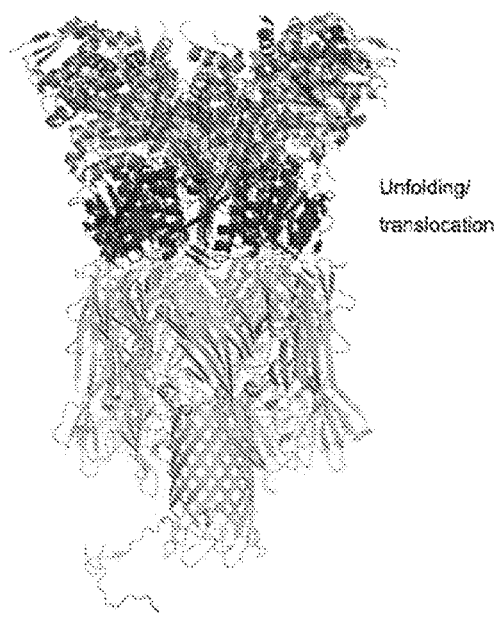
Figure 10F:
FIG. 10F illustrates that substrate protein is free to refold upon exit of the nanopore.

We note that voltage-driven translocation of all three model proteins was observed absent ClpX/ATP (FIG. 4). However, these ClpX-minus translocation events lacked the diagnostic ramping states shown in FIG. 2, and they were significantly longer and more variable in duration than were ClpX-mediated translocation events (FIG. 3C, FIG. 8, and FIG. 9). This is consistent with an unregulated translocation process dependent upon random structural fluctuations of the captured protein molecule and intermittent electrical force acting on a polymer with variable charge density. This contrasts with the relatively constant ATP hydrolysis rate and mechanical force imparted by the ClpX motor.

SEQUENCE LIST:

SEQ ID NO 1:
GGSSGGSGGSGSSGDGGSSGGSGGSGSSGDGGSSGGSGGDGSSGDGGSDG
DSDGSDGDGDSDGDDAANDENYALAA

SEQ ID NO 2:
GGSGSGGSGSGSGSGSQNEYRSGGSGSGGSGSGGSG

SEQ ID NO 3:
GGSGSAGSGASGSSGSEGSGASGSAGSGSAGSRGSGASGSAGSGSAGSGG
AEAAKEAAKEAAKEAAKEAAKAGGSGSAGSAGSASSGSDGSGASGSAGSG
SAGSKGSGASGSAGSGSSGS

SEQ ID NO 4 (S1): MGSSHHHHHHGSG ← black
LVPRGSASMSDSEVNQEAKPEVKPEVKPETHINLKVSDGSSEIFFKIKKT
TPLRRLMEAFAKRQGKEMDSLRFLYDGIRIQADQTPEDLDMEDNDIIEAH
REQIGG ← green
GGSSGGSGGSGSSGDGGSSGGSGGSGSSGDGGSSGGSGGDGSSGDGGSDG
DSDGSDGDGDSDGDD ← yellow
AANDENYALAA ← red SEQ ID NO 5 (S2-35):
MGHHHHHHGS ← black
LQDSEVNQEAKPEVKPEVKPETHINLKVSDGSSEIFFKIKKTTPLRRLME
AFAKRQGKEMDSLRFLYDGIRIQADQAPEDLDMEDNDIIEAHREQIGGGG
SGSGGSGSGGSGSQNEYRSGGSGSGGSGSGGSG ← green
MGSSHHHHHHGSG ← black
LVPRGSASMSDSEVNQEAKPEVKPEVKPETHINLKVSDGSSEIFFKIKKT
TPLRRLMEAFAKRQGKEMDSLRFLYDGIRIQADQTPEDLDMEDNDIIEAH
REQIGG ← green
GGSSGGSGGSGSSGDGGSSGGSGGSGSSGDGGSSGGSGGDGSSGDGGSDG
DSDGSDGDGDSDGDD ← yellow
AANDENYALAA ← red SEQ ID NO 6 (S2-148):
MGHHHHHHGS ← black
LQDSEVNQEAKPEVKPEVKPETHINLKVSDGSSEIFFKIKKTTPLRRLME
AFAKRQGKEMDSLRFLYDGIRIQADQAPEDLDMEDNDIIEAHREQIG
G ← green
GGSGSGGSGSGGSGSQNEYRSGGGGSGSAGSGASGSSGSEGSGASGSAGS
GSAGSRGSGASGSAGSGSAGSGGAEAAKEAAKEAAKEAAKEAAKAGGSGS
AGSAGSASSGSDGSGASGSAGSGSAGSKGSGASGSAGSGSSGSSGGS
G ← orange
MGSSHHHHHHGSG ← black
LVPRGSASMSDSEVNQEAKPEVKPEVKPETHINLKVSDGSSEIFFKIKKT
TPLRRLMEAFAKRQGKEMDSLRFLYDGIRIQADQTPEDLDMEDNDIIEAH
REQIGG ← green
GGSSGGSGGSGSSGDGGSSGGSGGSGSSGDGGSSGGSGGDGSSGDGGSDG
DSDGSDGDGDSDGDD ← yellow
AANDENYALAA ← red S1-RQA:
MGSSHHHHHHGSG ← black
LVPRGSASMSDSEVNQEAKPEVKPEVKPETHINLKVSDGSSEIFFKIKKT
TPLRRLMEAFAKRQGKEMDSLRFLYDGIRIQADQTPEDLDMEDNDIIEAH
REQIGG ← green
GGSSGGSGGSGSSGDGGSSGGSGGSGSSGDGGSSGGSGGDGSSGDGGSDG
DSDGSDGDGDSDGDD ← yellow
AANDENYALAA ← red
RQA ← blue COLOR CODE: Green: Smt3 domains; yellow: charged tail; red: ssrA tag; orange: linker region; black: affinity purification tag regions; blue: additional residues added to obscure the ssrA tag.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

What is claimed is:

1. A method of determining one or more characteristics of a protein, comprising the steps of:
   (a) providing a device for translocating a protein through a nanopore, comprising:
      (i) a nanopore in a membrane separating a fluidic chamber into a *cis* side and a *trans* side; and
      (ii) a circuit for providing a voltage between the *cis* side and the *trans* side and for monitoring ionic current flowing through the nanopore;
   (b) adding to said fluidic chamber a ring-shaped nucleoside triphosphate (NTP) driven unfoldase;
   (c) adding a protein to the *cis* side, wherein the protein comprises a sequence exogenous to the protein;
   (d) allowing the protein to contact the ring-shaped NTP driven unfoldase;
   (e) allowing the protein to be translocated by the ring-shaped NTP driven unfoldase through the ring-shaped NTP driven unfoldase and through the nanopore to the *trans* side;
   (f) monitoring ionic current changes during translocation of the protein through the nanopore; and
   (g) determining one or more characteristics of the protein based on the ionic current changes.

2. The method of claim 1 further comprising monitoring ionic current changes for states of (i) open channel, (ii) capture of the protein by the nanopore, and (iii) passage of the protein from (ii) through the nanopore.

3. The method of claim 2 comprising detecting differences between states (i), (ii) and (iii).

4. The method of claim 2 comprising monitoring a state of binding of the ring-shaped NTP driven unfoldase to the protein and translocation of the protein toward the nanopore, which occurs as a state between states (ii) and (iii).

5. The method of claim 1 wherein the nanopore is a pore protein.

6. The method of claim 5 wherein the nanopore is α-hemolysin.

7. The method of claim 1 wherein the ring-shaped NTP driven unfoldase is attached to the nanopore.

8. The method of claim 1 wherein the ring-shaped NTP driven unfoldase is an ATPases Associated with diverse cellular Activities (AAA+) enzyme.

9. The method of claim 1 wherein the circuit comprises a patch clamp amplifier applying a constant voltage between the *cis* chamber and the *trans* chamber.

10. The method of claim 1 wherein the protein is added in a non-denatured state.

11. The method of claim 2 wherein the protein is added in a non-denatured state.

12. The method of claim 8 wherein the AAA+ enzyme is ClpX.

13. The method of claim 5 wherein the nanopore is Mycobacteria *smegmatis* porin A (MspA).

14. The method of claim 1 wherein the one or more characteristics comprises the identity of the protein.

15. The method of claim 1 wherein the one or more characteristics comprises a sequence of the protein.

16. The method of claim 1 wherein the exogenous sequence comprises a targeting domain for the ring-shaped NTP driven unfoldase.

17. The method of claim 1 wherein the nanopore is a solid-state pore.

* * * * *

SEQUENCE LISTING

<160> NUMBER OF SEQ ID NOS: 8

<210> SEQ ID NO 1
<211> LENGTH: 76
<212> TYPE: PRT
<213> ORGANISM: artificial sequence
<220> FEATURE:
<223> OTHER INFORMATION: synthetic

<400> SEQUENCE: 1

Gly Gly Ser Ser Gly Gly Ser Gly Ser Gly Ser Ser Gly Asp Gly
1               5                   10                  15

Gly Ser Ser Gly Gly Ser Gly Ser Gly Ser Ser Gly Asp Gly Gly
                20                  25                  30

Ser Ser Gly Gly Ser Gly Gly Asp Gly Ser Ser Gly Asp Gly Gly Ser
            35                  40                  45

Asp Gly Asp Ser Asp Gly Ser Asp Gly Asp Gly Ser Asp Gly Asp
    50                  55                  60

Asp Ala Ala Asn Asp Glu Asn Tyr Ala Leu Ala Ala
65                  70                  75

<210> SEQ ID NO 2
<211> LENGTH: 35
<212> TYPE: PRT
<213> ORGANISM: artificial sequence
<220> FEATURE:
<223> OTHER INFORMATION: synthetic

<400> SEQUENCE: 2

Gly Gly Ser Gly Ser Gly Gly Ser Gly Ser Gly Gly Ser Gly Ser Gln
1               5                   10                  15

Asn Glu Tyr Arg Ser Gly Gly Ser Gly Ser Gly Gly Ser Gly Ser Gly
                20                  25                  30

Gly Ser Gly
        35

<210> SEQ ID NO 3
<211> LENGTH: 120
<212> TYPE: PRT
<213> ORGANISM: artificial sequence
<220> FEATURE:
<223> OTHER INFORMATION: synthetic

<400> SEQUENCE: 3

Gly Gly Ser Gly Ser Ala Gly Ser Gly Ala Ser Gly Ser Ser Gly Ser
1               5                   10                  15

Glu Gly Ser Gly Ala Ser Gly Ser Ala Gly Ser Gly Ser Ala Gly Ser
                20                  25                  30

Arg Gly Ser Gly Ala Ser Gly Ser Ala Gly Ser Gly Ser Ala Gly Ser
            35                  40                  45

Gly Gly Ala Glu Ala Ala Lys Glu Ala Ala Lys Glu Ala Ala Lys Glu
    50                  55                  60

Ala Ala Lys Glu Ala Ala Lys Ala Gly Ser Gly Ser Ala Gly Ser
65                  70                  75                  80

Ala Gly Ser Ala Ser Ser Gly Ser Asp Gly Gly Ala Ser Gly Ser
                85                  90                  95

Ala Gly Ser Gly Ser Ala Gly Ser Lys Gly Ser Gly Ala Ser Gly Ser
            100                 105                 110

Ala Gly Ser Gly Ser Ser Gly Ser
        115                 120

```
<210> SEQ ID NO 4
<211> LENGTH: 195
<212> TYPE: PRT
<213> ORGANISM: artificial sequence
<220> FEATURE:
<223> OTHER INFORMATION: synthetic

<400> SEQUENCE: 4

Met Gly Ser Ser His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Gly Gly Ser Gly Gly Ser Gly Gly
        115                 120                 125

Ser Gly Ser Ser Gly Asp Gly Gly Ser Ser Gly Gly Ser Gly Gly Ser
130                 135                 140

Gly Ser Ser Gly Asp Gly Gly Ser Ser Gly Gly Ser Gly Gly Asp Gly
145                 150                 155                 160

Ser Ser Gly Asp Gly Gly Ser Asp Gly Asp Ser Asp Gly Ser Asp Gly
                165                 170                 175

Asp Gly Asp Ser Asp Gly Asp Asp Ala Ala Asn Asp Glu Asn Tyr Ala
            180                 185                 190

Leu Ala Ala
        195

<210> SEQ ID NO 5
<211> LENGTH: 338
<212> TYPE: PRT
<213> ORGANISM: artificial sequence
<220> FEATURE:
<223> OTHER INFORMATION: synthetic

<400> SEQUENCE: 5

Met Gly His His His His His His Gly Ser Leu Gln Asp Ser Glu Val
1               5                   10                  15

Asn Gln Glu Ala Lys Pro Glu Val Lys Pro Glu Val Lys Pro Glu Thr
            20                  25                  30

His Ile Asn Leu Lys Val Ser Asp Gly Ser Ser Glu Ile Phe Phe Lys
        35                  40                  45

Ile Lys Lys Thr Thr Pro Leu Arg Arg Leu Met Glu Ala Phe Ala Lys
50                  55                  60

Arg Gln Gly Lys Glu Met Asp Ser Leu Arg Phe Leu Tyr Asp Gly Ile
65                  70                  75                  80

Arg Ile Gln Ala Asp Gln Ala Pro Glu Asp Leu Asp Met Glu Asp Asn
                85                  90                  95

Asp Ile Ile Glu Ala His Arg Glu Gln Ile Gly Gly Gly Gly Ser Gly
```

```
                100                 105                 110
Ser Gly Gly Ser Gly Ser Gly Gly Ser Gly Ser Gln Asn Glu Tyr Arg
            115                 120                 125

Ser Gly Gly Ser Gly Ser Gly Gly Ser Gly Ser Gly Gly Ser Gly Met
            130                 135                 140

Gly Ser Ser His His His His His Gly Ser Gly Leu Val Pro Arg
145                 150                 155                 160

Gly Ser Ala Ser Met Ser Asp Ser Glu Val Asn Gln Glu Ala Lys Pro
                165                 170                 175

Glu Val Lys Pro Glu Val Lys Pro Glu Thr His Ile Asn Leu Lys Val
            180                 185                 190

Ser Asp Gly Ser Ser Glu Ile Phe Phe Lys Ile Lys Lys Thr Thr Pro
            195                 200                 205

Leu Arg Arg Leu Met Glu Ala Phe Ala Lys Arg Gln Gly Lys Glu Met
            210                 215                 220

Asp Ser Leu Arg Phe Leu Tyr Asp Gly Ile Arg Ile Gln Ala Asp Gln
225                 230                 235                 240

Thr Pro Glu Asp Leu Asp Met Glu Asp Asn Asp Ile Ile Glu Ala His
                245                 250                 255

Arg Glu Gln Ile Gly Gly Gly Ser Ser Gly Ser Gly Gly Ser Gly Ser
            260                 265                 270

Gly Ser Ser Gly Asp Gly Gly Ser Ser Gly Gly Ser Gly Gly Ser Gly
            275                 280                 285

Ser Ser Gly Asp Gly Gly Ser Ser Gly Gly Ser Gly Gly Asp Gly Ser
290                 295                 300

Ser Gly Asp Gly Gly Ser Asp Gly Asp Ser Asp Gly Ser Asp Gly Asp
305                 310                 315                 320

Gly Asp Ser Asp Gly Asp Ala Ala Asn Asp Glu Asn Tyr Ala Leu
                325                 330                 335

Ala Ala

<210> SEQ ID NO 6
<211> LENGTH: 451
<212> TYPE: PRT
<213> ORGANISM: artificial sequence
<220> FEATURE:
<223> OTHER INFORMATION: synthetic

<400> SEQUENCE: 6

Met Gly His His His His His His Gly Ser Leu Gln Asp Ser Glu Val
1               5                   10                  15

Asn Gln Glu Ala Lys Pro Glu Val Lys Pro Glu Val Lys Pro Glu Thr
                20                  25                  30

His Ile Asn Leu Lys Val Ser Asp Gly Ser Ser Glu Ile Phe Phe Lys
            35                  40                  45

Ile Lys Lys Thr Thr Pro Leu Arg Arg Leu Met Glu Ala Phe Ala Lys
        50                  55                  60

Arg Gln Gly Lys Glu Met Asp Ser Leu Arg Phe Leu Tyr Asp Gly Ile
65                  70                  75                  80

Arg Ile Gln Ala Asp Gln Ala Pro Glu Asp Leu Asp Met Glu Asp Asn
                85                  90                  95

Asp Ile Ile Glu Ala His Arg Glu Gln Ile Gly Gly Gly Ser Gly
            100                 105                 110

Ser Gly Gly Ser Gly Ser Gly Gly Ser Gly Ser Gln Asn Glu Tyr Arg
            115                 120                 125
```

Ser Gly Gly Gly Gly Ser Gly Ser Ala Gly Ser Gly Ala Ser Gly Ser
            130                 135                 140

Ser Gly Ser Glu Gly Ser Gly Ala Ser Gly Ser Ala Gly Ser Gly Ser
145                 150                 155                 160

Ala Gly Ser Arg Gly Ser Gly Ala Ser Gly Ser Ala Gly Ser Gly Ser
            165                 170                 175

Ala Gly Ser Gly Gly Ala Glu Ala Ala Lys Glu Ala Ala Lys Glu Ala
            180                 185                 190

Ala Lys Glu Ala Ala Lys Glu Ala Ala Lys Ala Gly Gly Ser Gly Ser
            195                 200                 205

Ala Gly Ser Ala Gly Ser Ala Ser Gly Ser Asp Gly Ser Gly Ala
            210                 215                 220

Ser Gly Ser Ala Gly Ser Gly Ser Ala Gly Ser Lys Gly Ser Gly Ala
225                 230                 235                 240

Ser Gly Ser Ala Gly Ser Gly Ser Ser Gly Ser Ser Gly Gly Ser Gly
            245                 250                 255

Met Gly Ser Ser His His His His His His Gly Ser Gly Leu Val Pro
            260                 265                 270

Arg Gly Ser Ala Ser Met Ser Asp Ser Glu Val Asn Gln Glu Ala Lys
            275                 280                 285

Pro Glu Val Lys Pro Glu Val Lys Pro Glu Thr His Ile Asn Leu Lys
            290                 295                 300

Val Ser Asp Gly Ser Ser Glu Ile Phe Phe Lys Ile Lys Lys Thr Thr
305                 310                 315                 320

Pro Leu Arg Arg Leu Met Glu Ala Phe Ala Lys Arg Gln Gly Lys Glu
            325                 330                 335

Met Asp Ser Leu Arg Phe Leu Tyr Asp Gly Ile Arg Ile Gln Ala Asp
            340                 345                 350

Gln Thr Pro Glu Asp Leu Asp Met Glu Asp Asn Asp Ile Ile Glu Ala
            355                 360                 365

His Arg Glu Gln Ile Gly Gly Gly Ser Ser Gly Gly Ser Gly Gly
            370                 375                 380

Ser Gly Ser Ser Gly Asp Gly Gly Ser Ser Gly Gly Ser Gly Gly Ser
385                 390                 395                 400

Gly Ser Ser Gly Asp Gly Gly Ser Ser Gly Gly Ser Gly Gly Asp Gly
            405                 410                 415

Ser Ser Gly Asp Gly Gly Ser Asp Gly Asp Ser Asp Gly Ser Asp Gly
            420                 425                 430

Asp Gly Asp Ser Asp Gly Asp Ala Ala Asn Asp Glu Asn Tyr Ala
            435                 440                 445

Leu Ala Ala
    450

<210> SEQ ID NO 7
<211> LENGTH: 198
<212> TYPE: PRT
<213> ORGANISM: artificial sequence
<220> FEATURE:
<223> OTHER INFORMATION: synthetic

<400> SEQUENCE: 7

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

```
Pro Glu Val Lys Pro Glu Val Lys Pro Glu Thr His Ile Asn Leu Lys
            35                  40                  45

Val Ser Asp Gly Ser Ser Glu Ile Phe Phe Lys Ile Lys Lys Thr Thr
 50                  55                  60

Pro Leu Arg Arg Leu Met Glu Ala Phe Ala Lys Arg Gln Gly Lys Glu
 65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Gly Ser Ser Gly Gly Ser Gly Gly
            115                 120                 125

Ser Gly Ser Ser Gly Asp Gly Gly Ser Ser Gly Gly Ser Gly Gly Ser
 130                 135                 140

Gly Ser Ser Gly Asp Gly Gly Ser Ser Gly Gly Ser Gly Gly Asp Gly
 145                 150                 155                 160

Ser Ser Gly Asp Gly Gly Ser Asp Gly Asp Ser Asp Gly Ser Asp Gly
                165                 170                 175

Asp Gly Asp Ser Asp Gly Asp Asp Ala Ala Asn Asp Glu Asn Tyr Ala
            180                 185                 190

Leu Ala Ala Arg Gln Ala
            195

<210> SEQ ID NO 8
<211> LENGTH: 1145
<212> TYPE: PRT
<213> ORGANISM: artificial
<220> FEATURE:
<223> OTHER INFORMATION: synthetic

<400> SEQUENCE: 8

Met Gly Ser Ser His His His His His His Ser Ser His Met Ser Ala
 1               5                  10                  15

Leu Pro Thr Pro His Glu Ile Arg Asn His Leu Asp Asp Tyr Val Ile
                20                  25                  30

Gly Gln Glu Gln Ala Lys Lys Val Leu Ala Val Ala Val Tyr Asn His
            35                  40                  45

Tyr Lys Arg Leu Arg Asn Gly Asp Thr Ser Asn Gly Val Glu Leu Gly
 50                  55                  60

Lys Ser Asn Ile Leu Leu Ile Gly Pro Thr Gly Ser Gly Lys Thr Leu
 65                  70                  75                  80

Leu Ala Glu Thr Leu Ala Arg Leu Leu Asp Val Pro Phe Thr Met Ala
                85                  90                  95

Asp Ala Thr Thr Leu Thr Glu Ala Gly Tyr Val Gly Glu Asp Val Glu
            100                 105                 110

Asn Ile Ile Gln Lys Leu Leu Gln Lys Cys Asp Tyr Asp Val Gln Lys
            115                 120                 125

Ala Gln Arg Gly Ile Val Tyr Ile Asp Glu Ile Asp Lys Ile Ser Arg
 130                 135                 140

Lys Ser Asp Asn Pro Ser Ile Thr Arg Asp Val Ser Gly Glu Gly Val
 145                 150                 155                 160

Gln Gln Ala Leu Leu Lys Leu Ile Glu Gly Thr Val Ala Ala Val Pro
                165                 170                 175

Pro Gln Gly Gly Arg Lys His Pro Gln Gln Glu Phe Leu Gln Val Asp
            180                 185                 190
```

```
Thr Ser Lys Ile Leu Phe Ile Cys Gly Gly Ala Phe Ala Gly Leu Asp
            195                 200                 205

Lys Val Ile Ser His Arg Val Glu Thr Gly Ser Gly Ile Gly Phe Gly
210                 215                 220

Ala Thr Val Lys Ala Lys Ser Asp Lys Ala Ser Glu Gly Glu Leu Leu
225                 230                 235                 240

Ala Gln Val Glu Pro Glu Asp Leu Ile Lys Phe Gly Leu Ile Pro Glu
                245                 250                 255

Phe Ile Gly Arg Leu Pro Val Val Ala Thr Leu Asn Glu Leu Ser Glu
                260                 265                 270

Glu Ala Leu Ile Gln Ile Leu Lys Glu Pro Lys Asn Ala Leu Thr Lys
            275                 280                 285

Gln Tyr Gln Ala Leu Phe Asn Leu Glu Gly Val Asp Leu Glu Phe Arg
290                 295                 300

Asp Glu Ala Leu Asp Ala Ile Ala Lys Lys Ala Met Ala Arg Lys Thr
305                 310                 315                 320

Gly Ala Arg Gly Leu Arg Ser Ile Val Glu Ala Ala Leu Leu Asp Thr
                325                 330                 335

Met Tyr Asp Leu Pro Ser Met Glu Asp Val Glu Lys Val Val Ile Asp
                340                 345                 350

Glu Ser Val Ile Asp Gly Gln Ser Lys Pro Leu Leu Ile Tyr Gly Lys
            355                 360                 365

Pro Glu Ala Gln Gln Ala Ser Gly Glu Ala Ser Gly Ala Gly Gly Ser
370                 375                 380

Glu Gly Gly Gly Ser Gly Gly Thr Ser Gly Ala Thr Met Ser Ala
385                 390                 395                 400

Leu Pro Thr Pro His Glu Ile Arg Asn His Leu Asp Asp Tyr Val Ile
                405                 410                 415

Gly Gln Glu Gln Ala Lys Lys Val Leu Ala Val Ala Val Tyr Asn His
            420                 425                 430

Tyr Lys Arg Leu Arg Asn Gly Asp Thr Ser Asn Gly Val Glu Leu Gly
            435                 440                 445

Lys Ser Asn Ile Leu Leu Ile Gly Pro Thr Gly Ser Gly Lys Thr Leu
450                 455                 460

Leu Ala Glu Thr Leu Ala Arg Leu Leu Asp Val Pro Phe Thr Met Ala
465                 470                 475                 480

Asp Ala Thr Thr Leu Thr Glu Ala Gly Tyr Val Gly Glu Asp Val Glu
                485                 490                 495

Asn Ile Ile Gln Lys Leu Leu Gln Lys Cys Asp Tyr Asp Val Gln Lys
            500                 505                 510

Ala Gln Arg Gly Ile Val Tyr Ile Asp Glu Ile Asp Lys Ile Ser Arg
            515                 520                 525

Lys Ser Asp Asn Pro Ser Ile Thr Arg Asp Val Ser Gly Glu Gly Val
530                 535                 540

Gln Gln Ala Leu Leu Lys Leu Ile Glu Gly Thr Val Ala Ala Val Pro
545                 550                 555                 560

Pro Gln Gly Gly Arg Lys His Pro Gln Gln Glu Phe Leu Gln Val Asp
                565                 570                 575

Thr Ser Lys Ile Leu Phe Ile Cys Gly Gly Ala Phe Ala Gly Leu Asp
            580                 585                 590

Lys Val Ile Ser His Arg Val Glu Thr Gly Ser Gly Ile Gly Phe Gly
            595                 600                 605
```

```
Ala Thr Val Lys Ala Lys Ser Asp Lys Ala Ser Glu Gly Glu Leu Leu
610             615                 620

Ala Gln Val Glu Pro Glu Asp Leu Ile Lys Phe Gly Leu Ile Pro Glu
625             630                 635                 640

Phe Ile Gly Arg Leu Pro Val Val Ala Thr Leu Asn Glu Leu Ser Glu
                645                 650                 655

Glu Ala Leu Ile Gln Ile Leu Lys Glu Pro Lys Asn Ala Leu Thr Lys
                660                 665                 670

Gln Tyr Gln Ala Leu Phe Asn Leu Gly Val Asp Leu Glu Phe Arg
                675                 680                 685

Asp Glu Ala Leu Asp Ala Ile Ala Lys Lys Ala Met Ala Arg Lys Thr
690                 695                 700

Gly Ala Arg Gly Leu Arg Ser Ile Val Glu Ala Leu Leu Asp Thr
705                 710                 715                 720

Met Tyr Asp Leu Pro Ser Met Glu Asp Val Glu Lys Val Val Ile Asp
                725                 730                 735

Glu Ser Val Ile Asp Gly Gln Ser Lys Pro Leu Leu Ile Tyr Gly Lys
                740                 745                 750

Pro Glu Ala Gln Gln Ala Ser Gly Glu Ala Ser Gly Ala Gly Gly Ser
                755                 760                 765

Glu Gly Gly Gly Ser Glu Gly Ser Ser Gly Ala Thr Met Ser Ala
770                 775                 780

Leu Pro Thr Pro His Glu Ile Arg Asn His Leu Asp Asp Tyr Val Ile
785                 790                 795                 800

Gly Gln Glu Gln Ala Lys Lys Val Leu Ala Val Ala Val Tyr Asn His
                805                 810                 815

Tyr Lys Arg Leu Arg Asn Gly Asp Thr Ser Asn Gly Val Glu Leu Gly
                820                 825                 830

Lys Ser Asn Ile Leu Leu Ile Gly Pro Thr Gly Ser Gly Lys Thr Leu
                835                 840                 845

Leu Ala Glu Thr Leu Ala Arg Leu Leu Asp Val Pro Phe Thr Met Ala
                850                 855                 860

Asp Ala Thr Thr Leu Thr Glu Ala Gly Tyr Val Gly Glu Asp Val Glu
865                 870                 875                 880

Asn Ile Ile Gln Lys Leu Leu Gln Lys Cys Asp Tyr Asp Val Gln Lys
                885                 890                 895

Ala Gln Arg Gly Ile Val Tyr Ile Asp Glu Ile Asp Lys Ile Ser Arg
                900                 905                 910

Lys Ser Asp Asn Pro Ser Ile Thr Arg Asp Val Ser Gly Glu Gly Val
                915                 920                 925

Gln Gln Ala Leu Leu Lys Leu Ile Glu Gly Thr Val Ala Ala Val Pro
930                 935                 940

Pro Gln Gly Gly Arg Lys His Pro Gln Gln Glu Phe Leu Gln Val Asp
945                 950                 955                 960

Thr Ser Lys Ile Leu Phe Ile Cys Gly Gly Ala Phe Ala Gly Leu Asp
                965                 970                 975

Lys Val Ile Ser His Arg Val Glu Thr Gly Ser Gly Ile Gly Phe Gly
                980                 985                 990

Ala Thr Val Lys Ala Lys Ser Asp Lys Ala Ser Glu Gly Glu Leu Leu
                995                 1000                1005

Ala Gln Val Glu Pro Glu Asp Leu Ile Lys Phe Gly Leu Ile Pro
        1010            1015                1020

Glu Phe Ile Gly Arg Leu Pro Val Val Ala Thr Leu Asn Glu Leu
```

-continued

```
            1025                1030                1035
Ser Glu Glu Ala Leu Ile Gln Ile Leu Lys Glu Pro Lys Asn Ala
        1040                1045                1050

Leu Thr Lys Gln Tyr Gln Ala Leu Phe Asn Leu Glu Gly Val Asp
        1055                1060                1065

Leu Glu Phe Arg Asp Glu Ala Leu Asp Ala Ile Ala Lys Lys Ala
        1070                1075                1080

Met Ala Arg Lys Thr Gly Ala Arg Gly Leu Arg Ser Ile Val Glu
        1085                1090                1095

Ala Ala Leu Leu Asp Thr Met Tyr Asp Leu Pro Ser Met Glu Asp
        1100                1105                1110

Val Glu Lys Val Val Ile Asp Glu Ser Val Ile Asp Gly Gln Ser
        1115                1120                1125

Lys Pro Leu Leu Ile Tyr Gly Lys Pro Glu Ala Gln Gln Ala Ser
        1130                1135                1140

Gly Glu
    1145
```